United States Patent
Zheng et al.

(10) Patent No.: US 12,054,554 B2
(45) Date of Patent: Aug. 6, 2024

(54) MONOCLONAL ANTIBODY AGAINST HUMAN 4-1BB, METHOD FOR PREPARING THE SAME, AND USE THEREOF

(71) Applicants: WUXI Biologics (Shanghai) Co., Ltd., Pudong New District (CN); Wuxi Biologics Ireland Limited, Dublin (IE); Open Monoclonal Technology, Inc., San Diego, CA (US)

(72) Inventors: Yong Zheng, Shanghai (CN); Jingjing Liu, Shanghai (CN); Jing Li, Shanghai (CN)

(73) Assignees: WUXI BIOLOGICS (SHANGHAI) CO., LTD., Shanghai (CN); WUXI BIOLOGICS IRELAND LIMITED, Dublin (IE); OPEN MONOCLONAL TECHNOLOGY, INC., San Diego, CA (US)

( * ) Notice: Subject to any disclaimer, the term of this patent is extended or adjusted under 35 U.S.C. 154(b) by 800 days.

(21) Appl. No.: 17/045,561

(22) PCT Filed: Apr. 10, 2019

(86) PCT No.: PCT/CN2019/082074
§ 371 (c)(1),
(2) Date: Oct. 6, 2020

(87) PCT Pub. No.: WO2019/196868
PCT Pub. Date: Oct. 17, 2019

(65) Prior Publication Data
US 2021/0230287 A1    Jul. 29, 2021

(30) Foreign Application Priority Data
Apr. 10, 2018 (WO) ............... PCT/CN2018/082486

(51) Int. Cl.
*C07K 16/28* (2006.01)
*A61K 39/00* (2006.01)
*A61P 35/00* (2006.01)

(52) U.S. Cl.
CPC .......... *C07K 16/2878* (2013.01); *A61P 35/00* (2018.01); *A61K 2039/505* (2013.01);
(Continued)

(58) Field of Classification Search
CPC ............ C07K 16/2878; C07K 2317/21; C07K 2317/33; C07K 2317/34; C07K 2317/92; A61P 35/00; A61K 2039/505
See application file for complete search history.

(56) References Cited

U.S. PATENT DOCUMENTS

| 7,138,500 B1 | 11/2006 | Goodwin et al. |
| 2013/0078240 A1 | 3/2013 | Ahrens et al. |

FOREIGN PATENT DOCUMENTS

| AR | 046094 A1 | 11/2005 |
| CN | 1566341 A | 1/2005 |

(Continued)

OTHER PUBLICATIONS

Vinay et al., (2016) Therapeutic potential of anti-CD137 (4-1BB) monoclonal antibodies, Expert Opinion on Therapeutic Targets, 20:3, 361-373, (Year: 2016).*
(Continued)

*Primary Examiner* — Aurora M Fontainhas
*Assistant Examiner* — Selam Berhane
(74) *Attorney, Agent, or Firm* — James S. Keddie; Bozicevic, Field & Francis LLP

(57) ABSTRACT

Provided are novel fully human monoclonal antibodies that bind to human 4-1BB. It also provides the methods of hybridoma generation using humanized rats, the nucleic acid molecules encoding the anti-4-1BB antibodies, vectors and
(Continued)

host cells used for the expression of anti-4-1BB antibodies. The invention further provides methods for validating the function of antibodies in vitro and the efficacy of antibodies in vivo. The antibodies of invention provide a very potent agent for the treatment of multiple cancers via modulating human immune function.

14 Claims, 10 Drawing Sheets

Specification includes a Sequence Listing.

(52) U.S. Cl.
CPC ...... *C07K 2317/21* (2013.01); *C07K 2317/33* (2013.01); *C07K 2317/34* (2013.01); *C07K 2317/92* (2013.01)

(56) References Cited

FOREIGN PATENT DOCUMENTS

| | | |
|---|---|---|
| CN | 106413751 A | 2/2017 |
| KR | 20040083918 A | 10/2004 |
| PE | 20050962 A1 | 11/2005 |
| SG | 120723 A1 | 4/2006 |
| WO | WO-96/32495 A1 | 10/1996 |
| WO | WO 2005/035584 A1 | 4/2005 |
| WO | WO-2015/179236 A1 | 11/2015 |
| WO | WO 2017/130076 A1 | 8/2017 |

OTHER PUBLICATIONS

Extended European Search Report mailed on Dec. 7, 2021, for EP Application No. 19 785 334.4, filed on Apr. 10, 2019, 12 pages.

* cited by examiner ved by SPR;

MONOCLONAL ANTIBODY AGAINST HUMAN 4-1BB, METHOD FOR PREPARING THE SAME, AND USE THEREOF

PRIORITY CLAIM

The present application is a U.S. National Phase application, filed under 35 U.S.C. § 371(c), of International Application No. PCT/CN2019/082074, filed Apr. 10, 2019, which claims priority to, and the benefit of, PCT Application Number PCT/CN2018/082486, filed Apr. 10, 2018, the entire contents of each of which are herein incorporated by reference.

SEQUENCE LISTING

The contents of the text file submitted electronically herewith are incorporated herein by reference in their entirety: a computer readable format copy of the Sequence Listing (filename: CCPI_015_00US_SeqList_ST25.txt, date recorded Oct. 5, 2020, file size 15 kb).

FIELD OF THE INVENTION

This application generally relates to antibodies. More specifically, the application relates to fully human monoclonal antibodies that bind to human 4-1BB, a method for preparing the same, and the use thereof.

BACKGROUND OF THE INVENTION 4-1BB (also known as CD137, TNFRSF9), a member of the tumor necrosis factor (TNF) receptor superfamily, is an activation-induced T cell costimulatory molecule. It is mainly expressed on activated CD4+ and CD8+ T cells, activated B cells, and natural killer (NK) cells, but can also be found on resting monocytes and dendritic cells. As a costimulatory molecule, 4-1BB is involved in the activation and survival of CD4+, CD8+, and NK cells. 4-1BB agonist therapies elicit diverse immune effector responses on both the innate and adaptive immune arms. In pre-clinical tumor models, 4-1BB monotherapy and combinational therapy with other immune modulators can establish durable anti-tumor T cell memory response, which makes this receptor an attractive target for cancer immunotherapy.

Growing evidence indicates that anti-4-1BB monoclonal antibodies possess strong anti-tumor properties. Anti-4-1BB agonist can strongly activate CD8+ T cells to produce interferon (IFN)-γ and induce cytolytic markers. CD4+ effector T cells can also be stimulated to expand and produce pro-inflammatory cytokines. The 4-1BB agonistic therapy may inhibit the differentiation of conventional effector cells into Tregs, as well as Treg function. The 4-1BB signaling induces maturation of dendritic cells leading to the up-regulation of B7 costimulatory ligands, increases DC survival, and boosts the production of inflammatory cytokines such as IL-6, IL-12, and IL-27.

There are some spaces for improvement for antibody against 4-1BB as a therapeutic agent. As an agonist against co-stimulatory receptor, the toxicity of agonistic 4-1BB antibody, such as cytokine storm, may be the most concerned issue, which limits its clinical applications. Moreover, the anti-4-1BB antibodies currently tested in clinical trials can only bind to human and cynomolgus monkey 4-1BB proteins, but not to mouse 4-1BB protein, which limits the preclinical in vivo model for testing the therapeutic efficacy and toxicity of the potential candidates.

In this invention, the inventors have generated fully human antibodies against 4-1BB utilizing proprietary hybridoma technology. The antibodies of this invention have high binding affinity, specifically bind to human, cynomolgus monkey as well as mouse 4-1BB protein; potently modulate immune responses, including enhancing T cell proliferation and increasing cytokine IFN-γ production; have superior anti-tumor activity; and extend survival ratio of a subject.

SUMMARY OF THE INVENTION

These and other objectives are provided for by the present invention which, in a broad sense, is directed to compounds, methods, compositions and articles of manufacture that provide antibodies with improved efficacy. The benefits provided by the present invention are broadly applicable in the field of antibody therapeutics and diagnostics and may be used in conjunction with antibodies that react with a variety of targets. The present invention provides antibodies, preferably fully human monoclonal antibodies, that bind to human 4-1BB. It also provides methods of hybridoma generation using humanized rats, nucleic acid molecules encoding the anti-4-1BB antibodies, vectors and host cells used for the expression of anti-4-1BB antibodies. The invention further provides the methods for validating the function of antibodies in vitro and in vivo. The antibodies of the invention provide a potent agent for the treatment of multiple diseases via modulating human immune function.

In some aspects, the invention comprises an isolated antibody, or an antigen-binding portion thereof.

In some embodiments, the isolated antibody or the antigen-binding portion thereof has one or more of the following properties:
  (a) binding human 4-1 in with a $K_D$ of $2\times10^{-10}$ M or less, as measured by SPR;
  (b) binding cynomolgus 4-1BB with a $K_D$ of $5\times10^{-10}$ M or less, as measured by SPR;
  (c) binding mouse 4-1BB with a $K_D$ of $3\times10^{-8}$ M or less, as measured by SPR;
  (d) inducing production of a cytokine (for example, IFN-γ) in CD4+ T cells;
  (e) enhancing T cell proliferation;
  (f) binding human, cynomolgus monkey or mouse 4-1BB respectively;
  (g) having no cross-reactivity to human OX40, CD40 or GITR; or
  (h) mediating no ADCC and/or CDC effect on activated human T cells.

In some embodiments, the isolated antibody or the antigen-binding portion thereof binds to at least one of the following residues: L112, T113, W136, T137, N138, V146, T151, or D155 of SEQ ID NO:21.

In some embodiments, the isolated antibody or the antigen-binding portion thereof comprises:
  A) one or more heavy chain CDRs (CDRHs) selected from at least one of the group consisting of: (i) a CDRH1 with at least 90% sequence identity to a CDRH1 as set forth in one of the sequences selected from the group consisting of SEQ ID NOs: 1 and 7; (ii) a CDRH2 with at least 90% sequence identity to a CDRH2 as set forth in one of the sequences selected from the group consisting of SEQ ID NOs: 2 and 8; and (iii) a CDRH3 with at least 90% sequence identity to a CDRH3 as set forth in one of the sequences selected from the group consisting of SEQ ID NOs: 3 and 9;

B) one or more light chain CDRs (CDRLs) selected from at least one of the group consisting of: (i) a CDRL1 with at least 90% sequence identity to a CDRL1 as set forth in one of the sequences selected from the group consisting of SEQ ID NOs: 4 and 10; (ii) a CDRL2 with at least 90% sequence identity to a CDRL2 as set forth in one of the sequences selected from the group consisting of SEQ ID NOs: 5 and 11; and (iii) a CDRL3 with at least 90% sequence identity to a CDRL3 as set forth in one of the sequences selected from the group consisting of SEQ ID NOs: 6 and 12; or C) one or more CDRHs of A) and one or more CDRLs of B).

In some embodiments, the isolated antibody or the antigen-binding portion thereof comprises:

A) one or more (such as 1, 2 or 3) heavy chain CDRs (CDRHs) selected from at least one of the group consisting of: (i) a CDRH1 selected from the group consisting of SEQ ID NOs: 1 and 7 or a CDRH1 that differs in amino acid sequence from the CDRH1 by an amino acid addition, deletion or substitution of not more than 2 amino acids; (ii) a CDRH2 selected from the group consisting of SEQ ID NOs: 2 and 8 or a CDRH2 that differs in amino acid sequence from the CDRH2 by an amino acid addition, deletion or substitution of not more than 2 amino acids; and (iii) a CDRH3 selected from the group consisting of SEQ ID NOs: 3 and 9 or a CDRH3 that differs in amino acid sequence from the CDRH3 by an amino acid addition, deletion or substitution of not more than 2 amino acids;

B) one or more (such as 1, 2 or 3) light chain CDRs (CDRLs) selected from at least one of the group consisting of: (i) a CDRL1 selected from the group consisting of SEQ ID NOs: 4 and 10 or a CDRL1 that differs in amino acid sequence from the CDRL1 by an amino acid addition, deletion or substitution of not more than 2 amino acids; (ii) a CDRL2 selected from the group consisting of SEQ ID NOs: 5 and 11 or a CDRL2 that differs in amino acid sequence from the CDRL2 by an amino acid addition, deletion or substitution of not more than 2 amino acids; (iii) a CDRL3 selected from the group consisting of SEQ ID NOs: 6 and 12 or a CDRL3 that differs in amino acid sequence from the CDRL3 by an amino acid addition, deletion or substitution of not more than 2 amino acids; or C) one or more CDRHs of A) and one or more CDRLs of B).

In some embodiments, the isolated antibody or the antigen-binding portion thereof comprises:

A) a CDRH3 comprising SEQ ID NO: 3 or 9; or

B) a CDRH3 with at least 90% sequence identity to a CDRH3 as set forth in one of the sequences selected from the group consisting of SEQ ID NOs: 3 and 9; or C) a CDRH3 that differs in amino acid sequence from the CDRH3 of (A) by an amino acid addition, deletion or substitution of not more than 2 amino acids, and wherein the isolated antibody or the antigen-binding portion thereof binds human 4-1BB with a $K_D$ of $2\times10^{-10}$ M or less.

In some embodiments, the isolated antibody or the antigen-binding portion thereof comprises:

(a) a CDRH1 comprising or consisting of SEQ ID NO: 1;
(b) a CDRH2 comprising or consisting of SEQ ID NO: 2;
(c) a CDRH3 comprising or consisting of SEQ ID NO: 3;
(d) a CDRL1 comprising or consisting of SEQ ID NO: 4;
(e) a CDRL2 comprising or consisting of SEQ ID NO: 5; and
(f) a CDRL3 comprising or consisting of SEQ ID NO: 6.

In some embodiments, the isolated antibody or the antigen-binding portion thereof comprises:

(a) a CDRH1 comprising or consisting of SEQ ID NO: 7;
(b) a CDRH2 comprising or consisting of SEQ ID NO: 8;
(c) a CDRH3 comprising or consisting of SEQ ID NO: 9;
(d) a CDRL1 comprising or consisting of SEQ ID NO: 10;
(e) a CDRL2 comprising or consisting of SEQ ID NO: 11; and
(f) a CDRL3 comprising or consisting of SEQ ID NO: 12.

In some embodiments, the isolated antibody or the antigen-binding portion thereof comprises:

(A) a heavy chain variable region:
(i) comprising the amino acid sequence of SEQ ID NO: 13;
(ii) comprising an amino acid sequence at least 85%, at least 90%, or at least 95% identical to SEQ ID NO: 13;
(iii) comprising an amino acid sequence with addition, deletion and/or substitution of one or more (such as 1-10, 1-5, 1-3, 1, 2, 3, 4, or 5) amino acids compared with SEQ ID NO: 13; and/or (B) a light chain variable region:
(i) comprising the amino acid sequence of SEQ ID NO: 14;
(ii) comprising an amino acid sequence at least 85%, at least 90%, or at least 95% identical to SEQ ID NO: 14; or
(iii) comprising an amino acid sequence with addition, deletion and/or substitution of one or more (such as 1-10, 1-5, 1-3, 1, 2, 3, 4, or 5) amino acids compared with SEQ ID NO: 14.

In some embodiments, the isolated antibody or the antigen-binding portion thereof comprises:

(A) a heavy chain variable region:
(i) comprising the amino acid sequence of SEQ ID NO: 15;
(ii) comprising an amino acid sequence at least 85%, at least 90%, or at least 95% identical to SEQ ID NO: 15; or
(iii) comprising an amino acid sequence with addition, deletion and/or substitution of one or more (such as 1-10, 1-5, 1-3, 1, 2, 3, 4, or 5) amino acids compared with SEQ ID NO: 15; and/or (B) a light chain variable region:
(i) comprising the amino acid sequence of SEQ ID NO: 16;
(ii) comprising an amino acid sequence at least 85%, at least 90%, or at least 95% identical to SEQ ID NO: 16; or
(iii) comprising an amino acid sequence with addition, deletion and/or substitution of one or more (such as 1-10, 1-5, 1-3, 1, 2, 3, 4, or 5) amino acids compared with SEQ ID NO: 16.

In some aspects, the invention is directed to an isolated nucleic acid molecule, comprising a nucleic acid sequence encoding the heavy chain variable region and/or the light chain variable region of the isolated antibody as disclosed herein.

In some aspects, the invention is directed to a vector comprising the nucleic acid molecule encoding the antibody or antigen-binding portion thereof as disclosed herein.

In some aspects, the invention is directed to a host cell comprising the expression vector as disclosed herein.

In some aspects, the invention is directed to a pharmaceutical composition comprising at least one antibody or antigen-binding portion thereof as disclosed herein and a pharmaceutically acceptable carrier.

In some aspects, the invention is directed to a method for preparing an anti-4-1BB antibody or antigen-binding portion thereof which comprises expressing the antibody or antigen-binding portion thereof in the host cell and isolating the antibody or antigen-binding portion thereof from the host cell.

In some aspects, the invention is directed to a method of modulating an immune response in a subject, comprising administering the antibody or antigen-binding portion thereof as disclosed herein to the subject such that an immune response in the subject is modulated.

In some aspects, the invention is directed to a method for treating abnormal cell growth in a subject, administering an effective amount of the antibody or antigen-binding portion thereof or the pharmaceutical composition as disclosed herein to the subject.

In some aspects, the invention is directed to a method for inhibiting growth of tumor cells in a subject, administering an effective amount of the antibody or antigen-binding portion thereof or the pharmaceutical composition as disclosed herein to the subject.

In some aspects, the invention is directed to a method for reducing tumor cell metastasis in a subject, administering an effective amount of the antibody or antigen-binding portion thereof or the pharmaceutical composition as disclosed herein to the subject.

In some aspects, the invention is directed to a method for treating or preventing proliferative disorders such as cancers in a subject comprising administering an effective amount of the antibody or antigen-binding portion thereof or the pharmaceutical composition as disclosed herein to the subject.

In some aspects, the invention is directed to the use of the antibody or antigen-binding portion thereof as disclosed herein in the manufacture of a medicament for treating or preventing proliferative disorders such as cancers.

In some aspects, the invention is directed to the use of the antibody or antigen-binding portion thereof as disclosed herein in the manufacture of a diagnostic agent for diagnosing proliferative disorders such as cancers.

In some aspects, the invention is directed to the antibody or antigen-binding portion thereof as disclosed herein for use in treating or preventing proliferative disorders such as cancers.

In some aspects, the invention is directed to kits or devices and associated methods that employ the antibody or antigen-binding portion thereof as disclosed herein, and pharmaceutical compositions as disclosed herein, which are useful for the treatment of proliferative disorders such as cancer. To this end the present invention preferably provides an article of manufacture useful for treating such disorders comprising a receptacle containing the antibody or antigen-binding portion thereof as disclosed herein and instructional materials for using the antibody or antigen-binding portion thereof as disclosed herein to treat, ameliorate or prevent a proliferative disorder or progression or recurrence thereof. In selected embodiments, the devices and associated methods will comprise the step of contacting at least one circulating tumor cell with the antibody or antigen-binding portion thereof as disclosed herein.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. Further, the contents of all references, patents and published patent applications cited throughout this application are incorporated herein in entirety by reference.

3-IgG1L or 2.19.8-u1-3-IgG4L (FIG. 17A) and 2.27.16-u1-1-IgG1L or 2.27.16-u1-1-IgG4L (FIG. 17B) to human 4-1BB, respectively.

Figure 18:
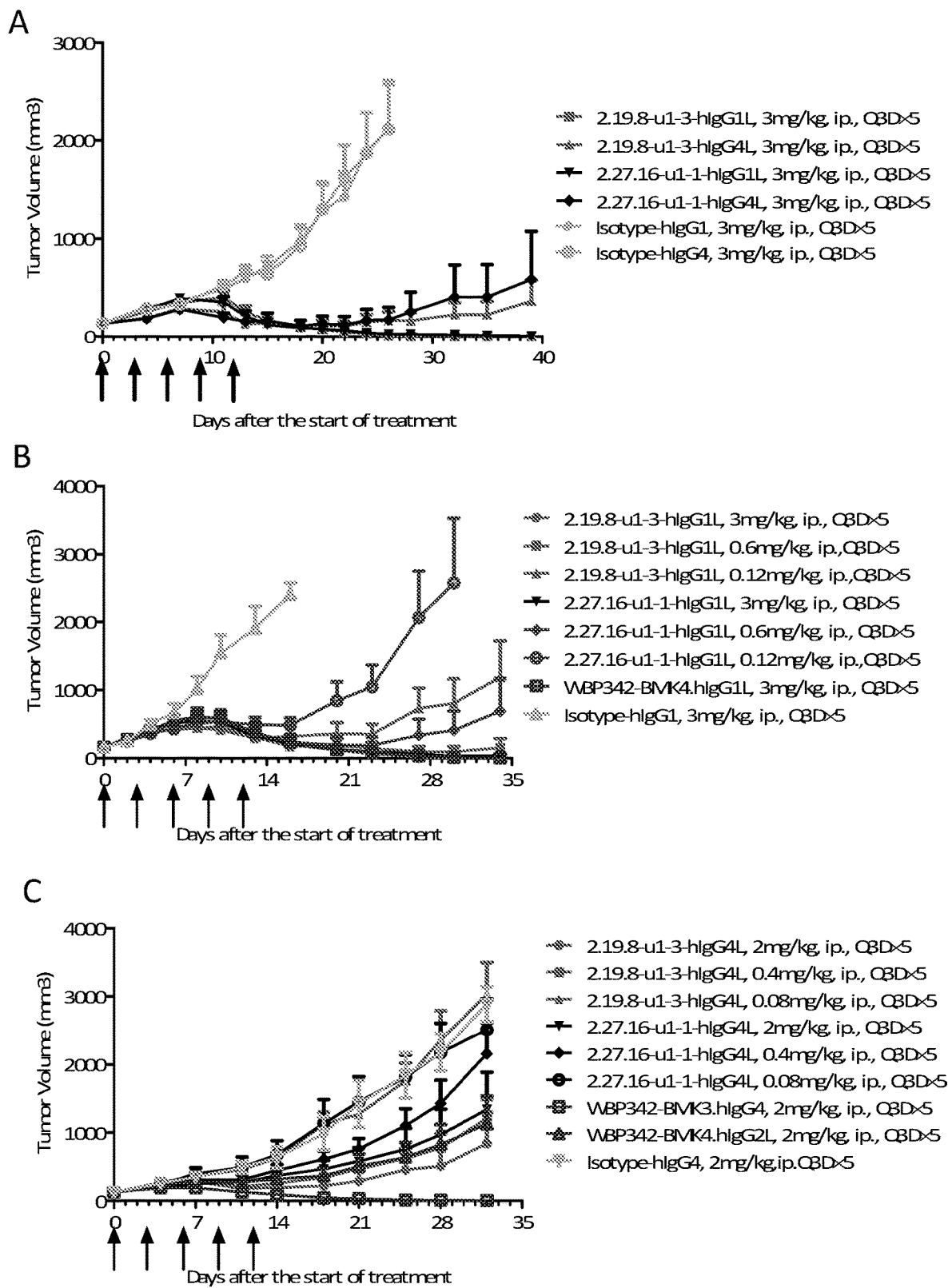

FIG. 18 shows the results of in vivo efficacy test of 4-1BB antibodies in B-h4-1BB transgenic mouse. As described in Example 6.1, mice burden with MC38 cells were treated with 4-1BB antibodies and the tumor size was measured twice weekly. FIG. 18A shows the effective inhibition of the 4-1BB antibodies against MC38 tumor growth, and FIGS. 18B and 18C show a dose-dependent anti-tumor effect of the 4-1BB antibodies.

DETAILED DESCRIPTION OF THE INVENTION

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In this application, the use of "or" means "and/or" unless stated otherwise. Furthermore, the use of the term "comprising," as well as other forms, such as "comprises" and "comprised," is not limiting. In addition, ranges provided in the specification and appended claims include both end points and all points between the end points.

Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Abbas et al., Cellular and Molecular Immunology, 6$^{th}$ ed., W.B. Saunders Company (2010); Sambrook J. & Russell D. *Molecular Cloning: A Laboratory Manual,* 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology,* Wiley, John & Sons, Inc. (2002); Harlow and Lane *Using Antibodies: A Laboratory Manual,* Cold Spring Harbor Laboratory Press, Cold Spring Harbor, N.Y. (1998); and Coligan et al., *Short Protocols in Protein Science,* Wiley, John & Sons, Inc. (2003). The nomenclature used in connection with, and the laboratory procedures and techniques of, analytical chemistry, synthetic organic chemistry, and medicinal and pharmaceutical chemistry described herein are those well-known and commonly used in the art. Moreover, any section headings used herein are for organizational purposes only and are not to be construed as limiting the subject matter described.

Definitions

In order to better understand the invention, the definitions and explanations of the relevant terms are provided as follows.

The term "antibody" or "Ab," as used herein, generally refers to a Y-shaped tetrameric protein comprising two heavy (H) and two light (L) polypeptide chains held together by covalent disulfide bonds and non-covalent interactions. Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a heavh chain, a variable region is linked to a constant region via a "J" region of about 12 or more amino acids, and a heavy chain further comprises a "D" region of about 3 or more amino acids. Each heavy chain consists of a heavy chain variable region (VH) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). $V_H$ and $V_L$ region can further be divided into hypervariable regions (called complementary determining regions (CDR)), which are interspaced by relatively conservative regions (called framework region (FR)). Each $V_H$ and VL consists of 3 CDRs and 4 FRs in the following order: FR1, CDR1, FR2, CDR2, FR3, CDR3, FR4 from N-terminal to C-terminal. The variable region ($V_H$ and $V_L$) of each heavy/light chain pair forms antigen binding sites, respectively. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196: 901-917; Chothia et al., (1989) Nature 342:878-883. Antibodies may be of different antibody isotypes, for example, IgG (e.g., IgG1, IgG2, IgG3 or IgG4 subtype), IgA1, IgA2, IgD, IgE or IgM antibody.

The term "antigen-binding portion" or "antigen-binding fragment" of an antibody, which can be interchangeably used in the context of the application, refers to polypeptides comprising fragments of a full-length antibody, which retain the ability of specifically binding to an antigen that the full-length antibody specifically binds to, and/or compete with the full-length antibody for binding to the same antigen. Generally, see Fundamental Immunology, Ch. 7 (Paul, W., ed., the second edition, Raven Press, N.Y. (1989), which is incorporated herein by reference for all purposes. Antigen binding fragments of an antibody may be produced by recombinant DNA techniques or by enzymatic or chemical cleavage of an intact antibody. Under some conditions, antigen binding fragments include Fab, Fab', F(ab')$_2$, Fd, Fv, dAb and complementary determining region (CDR) fragments, single chain antibody (e.g. scFv), chimeric antibody, diabody and such polypeptides that comprise at least part of antibody sufficient to confer the specific antigen binding ability on the polypeptides. Antigen binding fragments of an antibody may be obtained from a given antibody (e.g., the monoclonal anti-human 4-1BB antibody provided in the instant application) by conventional techniques known by a person skilled in the art (e.g., recombinant DNA technique or enzymatic or chemical cleavage methods), and may be screened for specificity in the same manner by which intact antibodies are screened.

The term "monoclonal antibody" or "mAb," as used herein, refer to a preparation of antibody molecules of single molecular composition. A monoclonal antibody displays a single binding specificity and affinity for a particular epitope.

The term "human antibody" or "fully human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody," as used herein, refers to antibodies displaying a single binding specificity, which have variable regions in which both the framework and CDR regions are derived from human germline immunoglobulin sequences.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody," as used herein, refers to an antibody in which the variable region sequences are derived from one species and the constant region sequences are derived from another species, such as an antibody in which the variable region sequences are derived from a mouse antibody and the constant region sequences are derived from a human antibody.

The term "recombinant antibody," as used herein, refers to an antibody that is prepared, expressed, created or isolated by recombinant means, such as antibodies isolated from an animal that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The term "anti-4-1BB antibody" or "4-1BB antibody, as used herein, refers to an antibody, as defined herein, capable of binding to a 4-1 BB receptor, for example, a human 4-1 BB receptor.

The terms "4-1BB," "4-1BB receptor," "4-1BB protein," "CD137" or "tumor necrosis factor receptor superfamily member 9 (TNFRSF9)," which are used interchangeably herein, is a member of the tumor necrosis factor (TNF) receptor superfamily, and is an activation-induced T cell costimulatory molecule. The term "4-1BB" may include human 4-1 BB receptor, as well as variants, isoforms, and species homologs thereof. Accordingly, an antibody or antigen-binding portion thereof, as defined and disclosed herein, may also bind 4-1 BB from species other than human, for example cynomolgus 4-1BB or mouse 4-1BB.

The term "human 4-1BB," as used herein, refers to human sequence 4-1BB, such as the complete amino acid sequence of human 4-1BB having Genbank Accession No. NP_001552.2. The human 4-1BB sequence may differ from human 4-1BB of Genbank Accession No. NP_001552.2 by having, e.g., conserved mutations or mutations in non-conserved regions and the 4-1BB has substantially the same biological function as the human 4-1BB of Genbank Accession No. NP_001552.2.

The term "mouse 4-1BB," as used herein, refers to mouse sequence 4-1BB, such as the complete amino acid sequence of mouse 4-1BB having Genbank Accession No. NP_035742.1.

The term "cynomolgus 4-1BB," as used herein, refers to cynomolgus sequence 4-1BB, such as the complete amino acid sequence of Rhesus macaque 4-1BB having Genbank Accession No. NP_001253057.1.

The term "Ka," as used herein, is intended to refer to the association rate of a particular antibody-antigen interaction, whereas the term "Kd" as used herein, is intended to refer to the dissociation rate of a particular antibody-antigen interaction. Kd values for antibodies can be determined using methods well established in the art. The term "$K_D$" as used herein, is intended to refer to the dissociation constant of a particular antibody-antigen interaction, which is obtained from the ratio of Kd to Ka (i.e., Kd/Ka) and is expressed as a molar concentration (M). A preferred method for determining the Kd of an antibody is by using surface plasmon resonance, preferably using a biosensor system such as a Biacore® system.

The term "high affinity" for an IgG antibody, as used herein, refers to an antibody having a $K_D$ of $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target antigen, for example, a 4-1BB receptor.

The term "$EC_{50}$," as used herein, which is also termed as "half maximal effective concentration" refers to the concentration of a drug, antibody or toxicant which induces a response halfway between the baseline and maximum after a specified exposure time. In the context of the application, $EC_{50}$ is expressed in the unit of "nM".

The term "compete for binding," as used herein, refers to the interaction of two antibodies in their binding to a binding target. A first antibody competes for binding with a second antibody if binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not, be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s).

The ability of "inhibit binding," as used herein, refers to the ability of an antibody or antigen-binding fragment thereof to inhibit the binding of two molecules (eg, human 4-1BB and human anti-4-1BB antibody) to any detectable level. In certain embodiments, the binding of the two molecules can be inhibited at least 50% by the antibody or antigen-binding fragment thereof. In certain embodiments, such an inhibitory effect may be greater than 60%, greater than 70%, greater than 80%, or greater than 90%.

The term "epitope," as used herein, refers to a portion on antigen that an immunoglobulin or antibody specifically binds to. "Epitope" is also known as "antigenic determinant". Epitope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein. Antibodies may be screened depending on competitiveness of binding to the same epitope by conventional techniques known by a person skilled in the art. For example, study on competition or cross-competition may be conducted to obtain antibodies that compete or cross-compete with each other for binding to antigens (e.g. RSV fusion protein). High-throughput methods for obtaining antibodies binding to the same epitope, which are based on their cross-competition, are described in an international patent application WO 03/48731.

The term "isolated," as used herein, refers to a state obtained from natural state by artificial means. If a certain "isolated" substance or component is present in nature, it is possible because its natural environment changes, or the substance is isolated from natural environment, or both. For example, a certain un-isolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other unpure substances that do not affect the activity of the isolated substance.

The term "isolated antibody," as used herein, is intended to refer to an antibody that is substantially free of other antibodies having different antigenic specificities (e.g., an isolated antibody that specifically binds a 4-1BB protein is substantially free of antibodies that specifically bind antigens other than 4-1BB proteins). An isolated antibody that specifically binds a human 4-1BB protein may, however, have cross-reactivity to other antigens, such as 4-1BB proteins from other species. Moreover, an isolated antibody can be substantially free of other cellular material and/or chemicals.

The term "vector," as used herein, refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

The term "host cell," as used herein, refers to a cellular system which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; or human tissues or hybridoma cells, yeast cells, and insect cells, and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell."

The term "identity," as used herein, refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al, 1988, SIAMJ. Applied Math. 48:1073.

The term "immunogenicity," as used herein, refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

The term "transfection," as used herein, refers to the process by which nucleic acids are introduced into eukaryotic cells, particularly mammalian cells. Protocols and techniques for transfection include but not limited to lipid transfection and chemical and physical methods such as electroporation. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al, 1981, Gene 13:197. In a specific embodiment of the invention, human 4-1BB gene was transfected into 293F cells.

The term "hybridoma" and the term "hybridoma cell line," as used herein, may be used interchangeably. When the term "hybridoma" and the term "hybridoma cell line" are mentioned, they also include subclone and progeny cell of hybridoma.

The term "SPR" or "surface plasmon resonance," as used herein, refers to and includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 5 and Jönsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "fluorescence-activated cell sorting" or "FACS," as used herein, refers to a specialized type of flow cytometry. It provides a method for sorting a heterogeneous mixture of biological cells into two or more containers, one cell at a time, based upon the specific light scattering and fluorescent characteristics of each cell (FlowMetric. "Sorting Out Fluorescence Activated Cell Sorting". Retrieved 2017-11-09.). Instruments for carrying out FACS are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

The term "antibody-dependent cell-mediated cytotoxicity" or "ADCC," as used herein, refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The term "complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g. as described in Gazzano-Santoro et al., J. Immunol. Methods 202: 163 (1996), may be performed.

The term "subject" includes any human or nonhuman animal, preferably humans.

The term "cancer," as used herein, refers to any or a tumor or a malignant cell growth, proliferation or metastasis-mediated, solid tumors and non-solid tumors such as leukemia and initiate a medical condition.

The term "treatment," "treating" or "treated," as used herein in the context of treating a condition, pertains generally to treatment and therapy, whether of a human or an animal, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included. For cancer, "treating" may refer to dampen or slow the tumor or malignant cell growth, proliferation, or metastasis, or some combination thereof. For tumors, "treatment" includes removal of all or part of the tumor, inhibiting or slowing tumor growth and metastasis, preventing or delaying the development of a tumor, or some combination thereof.

The term "an effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen. For instance, the "an effective amount," when used in connection with treatment of 4-1BB-related diseases or conditions, refers to an antibody or antigen-binding portion thereof in an amount or concentration effective to treat the said diseases or conditions.

The term "prevent," "prevention" or "preventing," as used herein, with reference to a certain disease condition in a mammal, refers to preventing or delaying the onset of the disease, or preventing the manifestation of clinical or subclinical symptoms thereof.

The term "pharmaceutically acceptable," as used herein, means that the vehicle, diluent, excipient and/or salts thereof, are chemically and/or physically is compatible with other ingredients in the formulation, and the physiologically compatible with the recipient.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminium adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments now. Aluminum hydroxide adjuvant is more commonly used in clinical trials.

Anti-4-1BB Antibodies

In some aspects, the invention comprises an isolated antibody or an antigen-binding portion thereof.

In the context of the application, the "antibody" may include polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof, and derivatives thereof including Fc fusions and other modifications, and any other immunoreactive molecule so long as it exhibits preferential association or binding with a 4-1BB protein. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). In a preferred embodiment, the antibody is a monoclonal antibody. In a more preferred embodiment, the antibody is a human monoclonal antibody.

Human antibodies can be produced using various techniques known in the art. One technique is phage display in which a library of (preferably human) antibodies is synthesized on phages, the library is screened with the antigen of interest or an antibody-binding portion thereof, and the phage that binds the antigen is isolated, from which one may obtain the immune-reactive fragments. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., Barbas et al., *Proc. Natl. Acad. Sci. USA* 88:7978-7982 (1991)).

Human antibodies can also be made by introducing human immunoglobulin loci into transgenic animals, e.g., mice in which the endogenous immunoglobulin genes have been partially or completely inactivated and human immunoglobulin genes have been introduced. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and U.S. Pat. Nos. 6,075,181 and 6,150,584 regarding XenoMouse® technology; and Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boerner et al., *J. Immunol,* 147 (1):86-95 (1991); and U.S. Pat. No. 5,750,373.

Monoclonal antibodies can be prepared using a wide variety of techniques known in the art including hybridoma techniques, recombinant techniques, phage display technologies, transgenic animals (e.g., a XenoMouse®) or some combination thereof. For example, monoclonal antibodies can be produced using hybridoma and art-recognized biochemical and genetic engineering techniques such as described in more detail in An, Zhigiang (ed.) *Therapeutic Monoclonal Antibodies: From Bench to Clinic*, John Wiley and Sons, 1$^{st}$ ed. 2009; Shire et. al. (eds.) *Current Trends in Monoclonal Antibody Development and Manufacturing*, Springer Science+Business Media LLC, 1$^{st}$ ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981) each of which is incorporated herein in its entirety by reference. It should be understood that a selected binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also an antibody of this invention. In a preferred embodiment, the anti-human 4-1BB monoclonal antibody is prepared by using hybridoma.

Generation of Hybridomas Producing Human Monoclonal Antibodies of the Invention

To generate hybridomas producing the antibodies of the invention, for instance, human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. Generation of hybridomas is well-known in the art. See, e.g., Harlow and Lane (1988) Antibodies, A Laboratory Manual, Cold Spring Harbor Publications, New York.

Generation of Transfectomas Producing Monoclonal Antibodies of the Invention

Antibodies of the invention also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody chain genes. Such regulatory sequences are described, e.g., in Goeddel (Gene Expression Technology. Methods in Enzymology 185, Academic Press, San Diego, CA (1990)). Exemplary regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe et al. (1988) MoI. Cell. Biol. 8:466-472). The expression vector and expression control sequences are chosen to be compatible with the expression host cell used.

The antibody light chain gene and the antibody heavy chain gene can be inserted into the same or separate expression vectors. In some embodiments, the variable regions are used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the invention can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Selectable marker genes may include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is possible to express the antibodies of the invention in either prokaryotic or eukaryotic host cells, for example, mammalian host cells, which can assemble and secrete a properly folded and immunologically active antibody.

Mammalian host cells for expressing the recombinant antibodies of the invention include Chinese Hamster Ovary (CHO cells) (including dhfr" CHO cells, described in Urlaub and Chasin, (1980) Proc. Natl. Acad. ScL USA 77:4216-4220, used with a DHFR selectable marker, e.g., as described in R. J. Kaufman and P. A. Sharp (1982) J. Mol. Biol. 159:601-621), NSO myeloma cells, COS cells and SP2 cells. In particular, for use with NSO myeloma cells, another expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, secretion of the antibody into the culture medium in which the host cells are grown. Antibodies can be recovered from the culture medium using standard protein purification methods.

Anti-4-1BB Antibodies with Certain Properties

The antibodies of the invention are characterized by particular functional features or properties of the antibodies.

In some embodiments, the isolated antibody or the antigen-binding portion thereof has one or more of the following properties:
(a) binding human 4-1BB with a $K_D$ of $2\times10^{-10}$ M or less, as measured by SPR;
(b) binding cynomolgus 4-1BB with a $K_D$ of $5\times10^{-10}$ M or less, as measured by SPR;
(c) binding mouse 4-1BB with a $K_D$ of $3\times10^{-8}$ M or less, as measured by SPR;
(d) inducing production of a cytokine (for example, IFN-γ) in CD4+ T cells;
(e) enhancing T cell proliferation;
(f) binding human, cynomolgus monkey or mouse 4-1BB respectively;
(gf) having no cross-reactivity to human OX40, CD40 or GITR; or
(h) mediating no ADCC and/or CDC effect on activated human T cells.

The antibody of the invention binds to human 4-1BB with high affinity. The binding of an antibody of the invention to 4-1BB can be assessed using one or more techniques well established in the art, for instance, ELISA. The binding specificity of an antibody of the invention can also be determined by monitoring binding of the antibody to cells expressing a 4-1BB protein, e.g., flow cytometry. For example, an antibody can be tested by a flow cytometry assay in which the antibody is reacted with a cell line that expresses human 4-1BB, such as CHO cells that have been transfected to express 4-1BB on their cell surface. Other suitable cells for use in flow cytometry assays include anti-CD3-stimulated CD4+ activated T cells, which express native 4-1BB. Additionally or alternatively, the binding of the antibody, including the binding kinetics (e.g., Kd value) can be tested in BIAcore binding assays. Still other suitable binding assays include ELISA assays, for example using a recombinant 4-1BB protein. For instance, an antibody of the invention binds to a human 4-1BB with a $K_D$ of $5\times10^{-10}$ M or less, binds to a human 4-1BB with a $K_D$ of $2\times10^{-10}$ M or less, binds to a human 4-1BB protein with a $K_D$ of $1\times10^{-10}$ M or less, binds to a human 4-1BB protein with a $K_D$ of $5\times10^{-11}$ M or less, binds to a human 4-1BB protein with a $K_D$ of $3\times10^{-11}$ M or less, or binds to a human 4-1BB protein with a $K_D$ of $2\times10^{-11}$ M or less.

The antibody of the invention also binds to mouse 4-1BB with high affinity. For instance, an antibody of the invention binds to a mouse 4-1BB with a $K_D$ of $1\times10^{-7}$ M or less, binds to a mouse 4-1BB with a $K_D$ of $5\times10^{-8}$ M or less, binds to a mouse 4-1BB protein with a $K_D$ of $3\times10^{-8}$ M or less, binds to a mouse 4-1BB protein with a $K_D$ of $2\times10^{-8}$ M or less, or binds to a mouse 4-1BB protein with a $K_D$ of $1\times10^{-8}$ M or less.

As for as known by the inventors, the anti-4-1BB antibodies available in the art can only bind to human and cynomolgus monkey 4-1BB proteins, but not to mouse 4-1BB protein, which limits the preclinical in vivo model for testing the therapeutic efficacy and toxicity of the potential candidates. In contrast, the anti-4-1BB antibodies of the invention bind to human, cynomolgus monkey as well as mouse 4-1BB protein with high affinity, and thus may provide preclinical in vivo model for testing the therapeutic efficacy and toxicity of the potential candidates.

Anti-4-1BB Antibodies Comprising CDRs with Sequence Identity to Specific Sequences In some embodiments, the isolated antibody or the antigen-binding portion thereof comprises:
A) one or more heavy chain CDRs (CDRHs) selected from at least one of the group consisting of: (i) a CDRH1 with at least 90% sequence identity to a CDRH1 as set forth in one of the sequences selected from the group consisting of SEQ ID NOs: 1 and 7; (ii) a CDRH2 with at least 90% sequence identity to a CDRH2 as set forth in one of the sequences selected from the group consisting of SEQ ID NOs: 2 and 8; and (iii) a CDRH3 with at least 90% sequence identity to a CDRH3 as set forth in one of the sequences selected from the group consisting of SEQ ID NOs: 3 and 9;

B) one or more light chain CDRs (CDRLs) selected from at least one of the group consisting of: (i) a CDRL1 with at least 90% sequence identity to a CDRL1 as set forth in one of the sequences selected from the group consisting of SEQ ID NOs: 4 and 10; (ii) a CDRL2 with at least 90% sequence identity to a CDRL2 as set forth in one of the sequences selected from the group consisting of SEQ ID NOs: 5 and 11; and (iii) a CDRL3 with at least 90% sequence identity to a CDRL3 as set forth in one of the sequences selected from the group consisting of SEQ ID NOs: 6 and 12; or C) one or more CDRHs of A) and one or more CDRLs of B).

The assignment of amino acids to each CDR may be in accordance with one of the numbering schemes provided by Kabat et al. (1991) *Sequences of Proteins of Immunological Interest* (5$^{th}$ Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies, 3$^{rd}$* Ed., Wily-VCH Verlag GmbH and Co. unless otherwise noted.

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, NY, 2001 and Dinarello et al., Current Protocols in Immunology, John Wiley and Sons Inc., Hoboken, N J, 2000. Exemplary databases of antibody sequences are described in, and can be accessed through, the "Abysis" website at www.bioinforg.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. See Dr. Andrew C. R. Martin's book chapter *Protein Sequence andStructure Analysis of Antibody Variable Domains*. In: *Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. Unless otherwise indicated, all CDRs set forth herein are derived according to the Abysis database website as per Kabat.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al, (1997) Nucleic Acids Res. 25(17):3389-3402. When utilizing BLAST and Gapped BLAST programs, the default parameters of the respective programs {e.g., XBLAST and NBLAST) can be used. See www.ncbi.nlm.nih.gov.

In other embodiments, the CDR amino acid sequences can be at least 90%, 91%, 92%, 93%, 94%, 95%, 96%, 97%, 98% or 99% identical to the respective sequences set forth above. As an illustrative example, the antibody may comprise a CDRH1 with at least 90%, 91%, 92%, 93%, 94%, 95%, 96%, 97%, 98% or 99% sequence identity to a CDRH1 as set forth in one of the sequences selected from the group consisting of SEQ ID NOs: 1 and 7.

Anti-4-1BB Antibodies Comprising CDRs with Amino Acid Addition, Deletion and/or Substitution In some embodiments, the isolated antibody or the antigen-binding portion thereof comprises:

A) one or more heavy chain CDRs (CDRHs) selected from at least one of the group consisting of: (i) a CDRH1 selected from the group consisting of SEQ ID NOs: 1 and 7 or a CDRH1 that differs in amino acid sequence from the CDRH1 by an amino acid addition, deletion or substitution of not more than 2 amino acids; (ii) a CDRH2 selected from the group consisting of SEQ ID NOs: 2 and 8 or a CDRH2 that differs in amino acid sequence from the CDRH2 by an amino acid addition, deletion or substitution of not more than 2 amino acids; and (iii) a CDRH3 selected from the group consisting of SEQ ID NOs: 3 and 9 or a CDRH3 that differs in amino acid sequence from the CDRH3 by an amino acid addition, deletion or substitution of not more than 2 amino acids;

B) one or more light chain CDRs (CDRLs) selected from at least one of the group consisting of: (i) a CDRL1 selected from the group consisting of SEQ ID NOs: 4 and 10 or a CDRL1 that differs in amino acid sequence from the CDRL1 by an amino acid addition, deletion or substitution of not more than 2 amino acids; (ii) a CDRL2 selected from the group consisting of SEQ ID NOs: 5 and 11 or a CDRL2 that differs in amino acid sequence from the CDRL2 by an amino acid addition, deletion or substitution of not more than 2 amino acids; and (iii) a CDRL3 selected from the group consisting of SEQ ID NOs: 6 and 12 or a CDRL3 that differs in amino acid sequence from the CDRL3 by an amino acid addition, deletion or substitution of not more than 2 amino acids; or C) one or more CDRHs of A) and one or more CDRLs of B).

Preferably, the CDRs of the isolated antibody or the antigen-binding portion thereof contain a conservative substitution of not more than 2 amino acids, or not more than 1 amino acid. The term "conservative substitution," as used herein, refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having 0-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

Anti-4-1BB Antibodies Comprising CDRs

In some embodiments, the isolated antibody or the antigen-binding portion thereof comprises:
(a) a CDRH1 comprising SEQ ID NO: 1;
(b) a CDRH2 comprising SEQ ID NO: 2;
(c) a CDRH3 comprising SEQ ID NO: 3;
(d) a CDRL1 comprising SEQ ID NO: 4;
(e) a CDRL2 comprising SEQ ID NO: 5; and
(f) a CDRL3 comprising SEQ ID NO: 6.

In a specific embodiment, the isolated antibody or the antigen-binding portion thereof comprises:
(a) a CDRH1 consisting of SEQ ID NO: 1;
(b) a CDRH2 consisting of SEQ ID NO: 2;
(c) a CDRH3 consisting of SEQ ID NO: 3;
(d) a CDRL1 consisting of SEQ ID NO: 4;
(e) a CDRL2 consisting of SEQ ID NO: 5; and
(f) a CDRL3 consisting of SEQ ID NO: 6.

In some embodiments, the isolated antibody or the antigen-binding portion thereof comprises:
(a) a CDRH1 comprising SEQ ID NO: 7;
(b) a CDRH2 comprising SEQ ID NO: 8;
(c) a CDRH3 comprising SEQ ID NO: 9;
(d) a CDRL1 comprising SEQ ID NO: 10;
(e) a CDRL2 comprising SEQ ID NO: 11; and
(f) a CDRL3 comprising SEQ ID NO: 12.

In a specific embodiment, the isolated antibody or the antigen-binding portion thereof comprises:
(a) a CDRH1 consisting of SEQ ID NO: 7;
(b) a CDRH2 consisting of SEQ ID NO: 8;
(c) a CDRH3 consisting of SEQ ID NO: 9;
(d) a CDRL1 consisting of SEQ ID NO: 10;
(e) a CDRL2 consisting of SEQ ID NO: 11; and
(f) a CDRL3 consisting of SEQ ID NO: 12.

Anti-4-1BB Antibodies Comprising a Heavy Chain Variable Region and a Light Chain Variable Region In some embodiments, the isolated antibody or the antigen-binding portion thereof comprises:
(A) a heavy chain variable region:
(i) comprising the amino acid sequence of SEQ ID NO: 13;
(ii) comprising an amino acid sequence at least 85%, at least 90%, or at least 95% identical to SEQ ID NO: 13; or
(iii) comprising an amino acid sequence with addition, deletion and/or substitution of one or more amino acids compared with SEQ ID NO: 13; and/or
(B) a light chain variable region:
(i) comprising the amino acid sequence of SEQ ID NO: 14;
(ii) comprising an amino acid sequence at least 85%, at least 90%, or at least 95% identical to SEQ ID NO: 14;
(iii) comprising an amino acid sequence with addition, deletion and/or substitution of one or more amino acids compared with SEQ ID NO: 14.

In a specific embodiment, the isolated antibody or the antigen-binding portion thereof comprises:
(a) a heavy chain variable region consisting of the amino acid sequence of SEQ ID NO: 13; and/or
(b) a light chain variable region comprising the amino acid sequence of SEQ ID NO: 14.

In some embodiments, the isolated antibody or the antigen-binding portion thereof comprises:
(A) a heavy chain variable region:
(i) comprising the amino acid sequence of SEQ ID NO: 15;
(ii) comprising an amino acid sequence at least 85%, at least 90%, or at least 95% identical to SEQ ID NO: 15; or
(iii) comprising an amino acid sequence with addition, deletion and/or substitution of one or more amino acids compared with SEQ ID NO: 15; and/or
(B) a light chain variable region:
(i) comprising the amino acid sequence of SEQ ID NO: 16;
(ii) comprising an amino acid sequence at least 85%, at least 90%, or at least 95% identical to SEQ ID NO: 16; or
(iii) comprising an amino acid sequence with addition, deletion and/or substitution of one or more amino acids compared with SEQ ID NO: 16.

In a specific embodiment, the isolated antibody or the antigen-binding portion thereof comprises:
(a) a heavy chain variable region consisting of the amino acid sequence of SEQ ID NO: 15; and/or
(b) a light chain variable region comprising the amino acid sequence of SEQ ID NO: 16.

In other embodiments, the amino acid sequences of the heavy chain variable region and/or the light chain variable region can be at least 85%, 86%, 87%, 88%, 89%, 90%, 91%, 92%, 93%, 94%, 95%, 96%, 97%, 98% or 99% identical to the respective sequences set forth above. As an illustrative example, the antibody may comprise a heavy chain variable region with at least 85%, 86%, 87%, 88%, 89%, 90%, 91%, 92%, 93%, 94%, 95%, 96%, 97%, 98% or 99% sequence identity to a heavy chain variable region consisting of the amino acid sequence of SEQ ID NO: 15.

In some further embodiments, the isolated antibody or the antigen-binding portion thereof may contain conservative substitution or modification of amino acids in the variable regions of the heavy chain and/or light chain. It is understood in the art that certain conservative sequence modification can be made which do not remove antigen binding. See, e.g., Brummell et al. (1993) Biochem 32:1180-8; de Wildt et al. (1997) Prot. Eng. 10:835-41; Komissarov et al. (1997) J. Biol. Chem. 272:26864-26870; Hall et al. (1992) J. Immunol. 149:1605-12; Kelley and O'Connell (1993) Biochem. 32:6862-35; Adib-Conquy et al. (1998) Int. Immunol. 10:341-6 and Beers et al. (2000) Clin. Can. Res. 6:2835-43.

As described above, the term "conservative substitution," as used herein, refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having 0-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

Binning and Epitope Mapping

It will further be appreciated the disclosed antibodies will associate with, or bind to, discrete epitopes or immunogenic determinants presented by the selected target or fragment thereof. In some embodiments, epitope or immunogenic determinants include chemically active surface groupings of molecules such as amino acids, sugar side chains, phosphoryl groups, or sulfonyl groups. In some embodiments, epitopes may have specific three-dimensional structural characteristics, and/or specific charge characteristics. Thus, as used herein the term "epitope" includes any protein determinant capable of specific binding to an immunoglobulin or T-cell receptor or otherwise interacting with a molecule. In some embodiments, an antibody is said to specifically bind (or immune-specifically bind or react) an antigen when it preferentially recognizes its target antigen in a complex mixture of proteins and/or macromolecules. In some embodiments, an antibody is said to specifically bind an antigen when the equilibrium dissociation constant ($K_D$) is less than or equal to $10^{-6}$ M or less than or equal to $10^{-7}$ M, more preferably when the e $K_D$ is less than or equal to $10^{-8}$ M, and even more preferably when the $K_D$ is less than or equal to $10^{-9}$ M.

Epitopes formed from contiguous amino acids (sometimes referred to as "linear" or "continuous" epitopes) are typically retained upon protein denaturing, whereas epitopes formed by tertiary folding are typically lost upon protein denaturing. In any event an antibody epitope typically includes at least 3, and more usually, at least 5 or 8-10 amino acids in a unique spatial conformation.

In this respect, it will be appreciated that, in some embodiments, an epitope may be associated with, or reside in, one or more regions, domains or motifs of, for example, the 4-1BB protein. Similarly, the art-recognized term "motif" will be used in accordance with its common meaning and shall generally refer to a short, conserved region of a protein that is typically ten to twenty contiguous amino acid residues.

In any event once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731. Other methods of binning or domain level or epitope mapping comprising antibody competition or antigen fragment expression on yeast are well known in the art.

As used herein, the term "binning" refers to methods used to group or classify antibodies based on their antigen binding characteristics and competition. While the techniques are useful for defining and categorizing the antibodies of the instant invention, the bins do not always directly correlate with epitopes and such initial determinations of epitope binding may be further refined and confirmed by other art-recognized methodology in the art and as described herein. However, it will be appreciated that empirical assignment of the antibodies to individual bins provides information that may be indicative of the therapeutic potential of the disclosed antibodies.

More specifically, one can determine whether a selected reference antibody (or fragment thereof) binds to the same epitope or cross competes for binding with a second test antibody (i.e., is in the same bin) by using methods known in the art and set forth in the Examples herein.

Other compatible epitope mapping techniques include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety).

Nucleic Acid Molecules Encoding Antibodies of the Invention

In some aspects, the invention is directed to an isolated nucleic acid molecule, comprising a nucleic acid sequence encoding the heavy chain variable region and/or the light chain variable region of the isolated antibody as disclosed herein.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

The isolated nucleic acid encoding the VH region can be converted to a full-length heavy chain gene by operatively linking the VH-encoding nucleic acid to another DNA molecule encoding heavy chain constant regions (CH1, CH2 and CH3). The sequences of human heavy chain constant region genes are known in the art (see e.g., Kabat et al. (1991), supra) and DNA fragments encompassing these regions can be obtained by standard PCR amplification. The heavy chain constant region can be an IgG1, IgG2, IgG3, IgG4, IgA, IgE, IgM or IgD constant region, but more preferably is an IgG1 or IgG4 constant region.

The isolated nucleic acid encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al., supra) and DNA fragments encompassing these regions can be obtained by standard PCR amplification. In preferred embodiments, the light chain constant region can be a kappa or lambda constant region.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

In some embodiments, the invention is directed to an isolated nucleic acid molecule, comprising a nucleic acid sequence encoding the heavy chain variable region of the isolated antibody as disclosed herein.

In some specific embodiments, the isolated nucleic acid molecule encodes the heavy chain variable region of the isolated antibody comprises a nucleic acid sequence selected from the group consisting of:
  (A) a nucleic acid sequence that encodes a heavy chain variable region as set forth in SEQ ID NO: 13 or 15;
  (B) a nucleic acid sequence as set forth in SEQ ID NO: 17 or 19; or
  (C) a nucleic acid sequence that hybridized under high stringency conditions to the complementary strand of the nucleic acid sequence of (B).

For example, the nucleic acid molecule is consisted of SEQ ID NO: 17 or 19. Alternatively, the nucleic acid molecule share an at least 80% (e.g. at least 85%, 86%, 87%, 88%, 89%, 90%, 91%, 92%, 93%, 94%, 95%, 96%, 97%, 98%, or 99%) sequence identity to SEQ ID NO: 17 or 19. In some specific embodiments, the percentage of identity is derived from the degeneracy of the genetic code, and the encoded protein sequences remain unchanged.

In some embodiments, the invention is directed to an isolated nucleic acid molecule, comprising a nucleic acid sequence encoding the light chain variable region of the isolated antibody as disclosed herein.

In some specific embodiments, the isolated nucleic acid molecule encodes the heavy chain variable region of the isolated antibody comprises a nucleic acid sequence selected from the group consisting of:
  (A) a nucleic acid sequence that encodes a heavy chain variable region as set forth in SEQ ID NO: 14 or 16;
  (B) a nucleic acid sequence as set forth in SEQ ID NO: 18 or 20; or
  (C) a nucleic acid sequence that hybridized under high stringency conditions to the complementary strand of the nucleic acid sequence of (B).

For example, the nucleic acid molecule is consisted of SEQ ID NO: 18 or 20. Alternatively, the nucleic acid molecule share an at least 80% (e.g. at least 85%, 86%, 87%, 88%, 89%, 90%, 91%, 92%, 93%, 94%, 95%, 96%, 97%, 98%, or 99%) sequence identity to SEQ ID NO: 18 or 20. In some specific embodiments, the percentage of identity is derived from the degeneracy of the genetic code, and the encoded protein sequences remain unchanged.

Exemplary high stringency conditions include hybridization at 45° C. in 5×SSPE and 45% formamide, and a final wash at 65° C. in 0.1×SSC. It is understood in the art that conditions of equivalent stringency can be achieved through variation of temperature and buffer, or salt concentration as described Ausubel, et al. (Eds.), Protocols in Molecular Biology, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al, (Eds.), Molecular Cloning: A laboratory Manual. Cold Spring Harbor Laboratory Press: Cold Spring Harbor, New York (1989), pp. 9.47 to 9.51.

Pharmaceutical Compositions

In some aspects, the invention is directed to a pharmaceutical composition comprising at least one antibody or antigen-binding portion thereof as disclosed herein and a pharmaceutically acceptable carrier.

Components of the Compositions

The pharmaceutical composition may optionally contain one or more additional pharmaceutically active ingredients, such as another antibody or a drug. The pharmaceutical compositions of the invention also can be administered in a combination therapy with, for example, another immune-stimulatory agent, anti-cancer agent, an antiviral agent, or a vaccine, such that the anti-4-1BB antibody enhances the immune response against the vaccine. A pharmaceutically acceptable carrier can include, for example, a pharmaceutically acceptable liquid, gel or solid carriers, an aqueous medium, a non-aqueous medium, an anti-microbial agent, isotonic agents, buffers, antioxidants, anesthetics, suspending/dispersing agent, a chelating agent, a diluent, adjuvant, excipient or a nontoxic auxiliary substance, other known in the art various combinations of components or more.

Suitable components may include, for example, antioxidants, fillers, binders, disintegrating agents, buffers, preservatives, lubricants, flavorings, thickening agents, coloring agents, emulsifiers or stabilizers such as sugars and cyclodextrin. Suitable anti-oxidants may include, for example, methionine, ascorbic acid, EDTA, sodium thiosulfate, platinum, catalase, citric acid, cysteine, mercapto glycerol, thioglycolic acid, Mercapto sorbitol, butyl methyl anisole, butylated hydroxy toluene and/or propylgalacte. As disclosed in the present invention, in a solvent containing an antibody or an antigen-binding fragment of the present invention discloses compositions include one or more anti-oxidants such as methionine, reducing antibody or antigen binding fragment thereof may be oxidized. The oxidation reduction may prevent or reduce a decrease in binding affinity, thereby enhancing antibody stability and extended shelf life. Thus, in some embodiments, the present invention provides a composition comprising one or more antibodies or antigen binding fragment thereof and one or more anti-oxidants such as methionine. The present invention further provides a variety of methods, wherein an antibody or antigen binding fragment thereof is mixed with one or more anti-oxidants, such as methionine, so that the antibody or antigen binding fragment thereof can be prevented from oxidation, to extend their shelf life and/or increased activity.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

Administration, Formulation and Dosage

The pharmaceutical composition of the invention may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Similarly, the particular dosage regimen, including dose, timing and repetition, will depend on the particular individual and that individual's medical history, as well as empirical considerations such as pharmacokinetics (e.g., half-life, clearance rate, etc.).

Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In some embodiments, the dosage administered may be adjusted or attenuated to manage potential side effects and/or toxicity. Alternatively, sustained continuous release formulations of a subject therapeutic composition may be appropriate.

It will be appreciated by one of skill in the art that appropriate dosages can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action that achieve the desired effect without causing substantial harmful or deleterious side-effects.

In general, the antibody or the antigen binding portion thereof of the invention may be administered in various ranges. These include about 5 µg/kg body weight to about 100 mg/kg body weight per dose; about 50 µg/kg body weight to about 5 mg/kg body weight per dose; about 100 µg/kg body weight to about 10 mg/kg body weight per dose. Other ranges include about 100 µg/kg body weight to about 20 mg/kg body weight per dose and about 0.5 mg/kg body weight to about 20 mg/kg body weight per dose. In certain embodiments, the dosage is at least about 100 µg/kg body weight, at least about 250 µg/kg body weight, at least about 750 g/kg body weight, at least about 3 mg/kg body weight, at least about 5 mg/kg body weight, at least about 10 mg/kg body weight.

In any event, the antibody or the antigen binding portion thereof of the invention is preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like.

In certain preferred embodiments, the course of treatment involving the antibody or the antigen-binding portion thereof of the instant invention will comprise multiple doses of the selected drug product over a period of weeks or months. More specifically, the antibody or the antigen-binding portion thereof of the instant invention may be administered once every day, every two days, every four days, every week, every ten days, every two weeks, every three weeks, every month, every six weeks, every two months, every ten weeks or every three months. In this regard, it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments, the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

Compatible formulations for parenteral administration (e.g., intravenous injection) will comprise the antibody or antigen-binding portion thereof as disclosed herein in concentrations of from about 10 µg/ml to about 100 mg/ml. In certain selected embodiments, the concentrations of the antibody or the antigen binding portion thereof will comprise 20 µg/ml, g/ml, 60 µg/ml, 80 µg/ml, 100 µg/ml, 200 µg/ml, 300, g/ml, 400 µg/ml, 500 µg/ml, 600 g/ml, 700 µg/ml, 800 µg/ml, 900 µg/ml or 1 mg/ml. In other preferred embodiments ADC concentrations will comprise 2 mg/ml, 3 mg/ml, 4 mg/ml, 5 mg/ml, 6 mg/ml, 8 mg/ml, 10 mg/ml, 12 mg/ml, 14 mg/ml, 16 mg/ml, 18 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml or 100 mg/ml Applications of the Invention The antibodies, antibody compositions and methods of the present invention have numerous in vitro and in vivo utilities involving, for example, detection of 4-1BB or enhancement of immune response. For example, these molecules can be administered to cells in culture, in vitro or ex vivo, or to human subjects, e.g., in vivo, to enhance immunity in a variety of situations. The immune response can be modulated, for instance, augmented, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-4-1BB antibodies can be administered together with an antigen of interest or the antigen may already be present in the subject to be treated (e.g., a tumor-bearing or virus-bearing subject). When antibodies to 4-1BB are administered together with another agent, the two can be administered in either order or simultaneously.

The invention further provides methods for detecting the presence of human 4-1BB antigen in a sample, or measuring the amount of human 4-1BB antigen, comprising contacting the sample, and a control sample, with a human monoclonal antibody, or an antigen binding portion thereof, which specifically binds to human 4-1BB, under conditions that allow for formation of a complex between the antibody or portion thereof and human 4-1BB. The formation of a complex is then detected, wherein a difference complex formation between the sample compared to the control sample is indicative of the presence of human 4-1BB antigen in the sample. Moreover, the anti-4-1BB antibodies of the invention can be used to purify human 4-1BB via immunoaffinity purification.

Treatment of Disorders Including Cancers

In some aspects, the present invention provides a method of treating a disorder in a mammal, which comprises administering to the subject (for example, a human) in need of treatment a therapeutically effective amount of the antibody or antigen-binding portion thereof. For example, the disorder is a cancer.

A variety of cancers where 4-1 BB is implicated, whether malignant or benign and whether primary or secondary, may be treated or prevented with a method provided by the disclosure. Examples of such cancers include lung cancers such as bronchogenic carcinoma (e.g., squamous cell carcinoma, small cell carcinoma, large cell carcinoma, and adenocarcinoma), alveolar cell carcinoma, bronchial adenoma, chondromatous hamartoma (noncancerous), and sarcoma (cancerous); colon cancer or colon carcinoma; heart cancer such as myxoma, fibromas, and rhabdomyomas; bone cancers such as osteochondromas, condromas, chondroblastomas, chondromyxoid fibromas, osteoid osteomas, giant cell tumors, chondrosarcoma, multiple myeloma, osteosarcoma, fibrosarcomas, malignant fibrous histiocytomas, Ewing's tumor (Ewing's sarcoma), and reticulum cell sarcoma; brain cancer such as gliomas (e.g., glioblastoma multiforme), anaplastic astrocytomas, astrocytomas, oligodendrogliomas, medulloblastomas, chordoma, Schwannomas, ependymomas, meningiomas, pituitary adenoma, pinealoma, osteomas, hemangioblastomas, craniopharyngiomas, chordomas, germinomas, teratomas, dermoid cysts, and angiomas; cancers in digestive system such as leiomyoma, epidermoid carcinoma, adenocarcinoma, leiomyosarcoma, stomach adenocarcinomas, intestinal lipomas, intestinal neurofibromas, intestinal fibromas, polyps in large intestine, and colorectal cancers; liver cancers such as hepatocellular adenomas, hemangioma, hepatocellular carcinoma, fibrolamellar carcinoma, cholangiocarcinoma, hepatoblastoma, and angiosarcoma; kidney cancers such as kidney adenocarcinoma, renal cell carcinoma, hypernephroma, and transitional cell carcinoma of the renal pelvis; bladder cancers; hematological cancers such as acute lymphocytic (lymphoblastic) leukemia, acute myeloid (myelocytic, myelogenous, myeloblasts, myelomonocytic) leukemia, chronic lymphocytic leukemia (e.g., Sezary syndrome and hairy cell leukemia), chronic myelocytic (myeloid, myelogenous, granulocytic) leukemia, Hodgkin's lymphoma, non-Hodgkin's lymphoma, B cell lymphoma, mycosis fungoides, and myeloproliferative disorders (including myeloproliferative disorders such as polycythemia vera, myelofibrosis, thrombocythemia, and chronic myelocytic leukemia); skin cancers such as basal cell carcinoma, squamous cell carcinoma, melanoma, Kaposi's sarcoma, and Paget's disease; head and neck cancers; eye-related cancers such as retinoblastoma and intraoccular melanocarcinoma; male reproductive system cancers such as benign prostatic hyperplasia, prostate cancer, and testicular cancers (e.g., seminoma, teratoma, embryonal carcinoma, and choriocarcinoma); breast cancer; female reproductive system cancers such as uterine cancer (endometrial carcinoma), cervical cancer (cervical carcinoma), cancer of the ovaries (ovarian carcinoma), vulvar carcinoma, vaginal carcinoma, fallopian tube cancer, and hydatidiform mole; thyroid cancer (including papillary, follicular, anaplastic, or medullary cancer); pheochromocytomas (adrenal gland); noncancerous growths of the parathyroid glands; pancreatic cancers; and hematological cancers such as leukemias, myelomas, non-Hodgkin's lymphomas, and Hodgkin's lymphomas. In a specific embodiment, the cancer is melanoma. In another specific embodiment, the cancer is colon carcinoma.

In some other embodiments, the disorder is an autoimmune disease. Examples of autoimmune diseases that may be treated with the antibody or antigen-binding portion thereof include autoimmune encephalomyelitis, lupus erythematosus, and rheumatoid arthritis. The antibody or the antigen-binding portion thereof may also be used to treat or prevent infectious disease, inflammatory disease (such as allergic asthma) and chronic graft-versus-host disease.

Stimulation of an Immune Response

In some aspects, the invention also provides a method of enhancing (for example, stimulating) an immune response in a subject comprising administering an antibody or an antigen binding portion thereof of the invention to the subject such that an immune response in the subject is enhanced. For example, the subject is a mammal. In a specific embodiment, the subject is a human.

The term "enhancing an immune response" or its grammatical variations, means stimulating, evoking, increasing, improving, or augmenting any response of a mammal's immune system. The immune response may be a cellular response (i.e. cell-mediated, such as cytotoxic T lymphocyte mediated) or a humoral response (i.e. antibody mediated response), and may be a primary or secondary immune response. Examples of enhancement of immune response include increased CD4+ helper T cell activity and generation of cytolytic T cells. The enhancement of immune response can be assessed using a number of in vitro or in vivo measurements known to those skilled in the art, including, but not limited to, cytotoxic T lymphocyte assays, release of cytokines (for example IL-2 production or IFN-7 production), regression of tumors, survival of tumor bearing animals, antibody production, immune cell proliferation, expression of cell surface markers, and cytotoxicity. Typically, methods of the disclosure enhance the immune response by a mammal when compared to the immune response by an untreated mammal or a mammal not treated using the methods as disclosed herein. In one embodiment, the antibody or an antigen binding portion thereof is used to enhance the immune response of a human to a microbial pathogen (such as a virus). In another embodiment, the antibody or an antigen binding portion thereof is used to enhance the immune response of a human to a vaccine. In one embodiment, the method enhances a cellular immune response, particularly a cytotoxic T cell response. In another embodiment, the cellular immune response is a T helper cell response. In still another embodiment, the immune response is a cytokine production, particularly IFN-7 production or IL-2 production. The antibody or an antigen binding portion thereof may be used to enhance the immune response of a human to a microbial pathogen (such as a virus) or to a vaccine.

The antibody or the antigen-binding portion thereof may be used alone as a monotherapy, or may be used in combination with chemical therapies or radiotherapies.

Combined Use with Chemotherapies

The antibody or the antigen-binding portion thereof may be used in combination with an anti-cancer agent, a cytotoxic agent or chemotherapeutic agent.

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with the disclosed site-specific antibodies prior to administration. More specifically, in certain embodiments selected anti-cancer agents will be linked to the unpaired cysteines of the engineered antibodies to provide engineered conjugates as set forth herein. Accordingly, such engineered conjugates are expressly contemplated as being within the scope of the instant invention. In other embodiments, the disclosed anti-cancer agents will be given in combination with site-specific conjugates comprising a different therapeutic agent as set forth above.

As used herein the term "cytotoxic agent" means a substance that is toxic to the cells and decreases or inhibits the function of cells and/or causes destruction of cells. In certain embodiments, the substance is a naturally occurring molecule derived from a living organism. Examples of cytotoxic agents include, but are not limited to, small molecule toxins or enzymatically active toxins of bacteria (e.g., Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *Saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the instant invention a "chemotherapeutic agent" comprises a chemical compound that nonspecifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI.

Examples of anti-cancer agents that may be used in combination with the site-specific constructs of the present invention (either as a component of a site specific conjugate or in an unconjugated state) include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, erlotinib, vemurafenib, crizotinib, sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, OR), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above.

Combined Use with Radiotherapies

The present invention also provides for the combination of the antibody or the antigen-binding portion thereof with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed conjugates may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

Diagnosis

The invention provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with an antibody as described herein and detecting presence or absence, or level of association, of the antibody to bound or free target molecules in the sample. In some embodiments, the antibody will comprise a detectable label or reporter molecule as described herein.

In some embodiments, the association of the antibody with particular cells in the sample can denote that the sample may contain tumorigenic cells, thereby indicating that the individual having cancer may be effectively treated with an antibody as described herein.

Samples can be analyzed by numerous assays, for example, radioimmunoassays, enzyme immunoassays (e.g. ELISA), competitive-binding assays, fluorescent immunoassays, immunoblot assays, Western Blot analysis and flow cytometry assays. Compatible in vivo theragnostic or diagnostic assays can comprise art recognized imaging or monitoring techniques, for example, magnetic resonance imaging, computerized tomography (e.g. CAT scan), positron tomography (e.g., PET scan), radiography, ultrasound, etc., as would be known by those skilled in the art.

Pharmaceutical Packs and Kits

Pharmaceutical packs and kits comprising one or more containers, comprising one or more doses of the antibody or the antigen-binding portion thereof are also provided. In certain embodiments, a unit dosage is provided wherein the unit dosage contains a predetermined amount of a composition comprising, for example, the antibody or the antigen-binding portion thereof, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the conjugate composition may be provided as a lyophilized powder that may be reconstituted upon addition of an appropriate liquid, for example, sterile water or saline solution. In certain preferred embodiments, the composition comprises one or more substances that inhibit protein aggregation, including, but not limited to, sucrose and arginine. Any label on, or associated with, the container(s) indicates that the enclosed conjugate composition is used for treating the neoplastic disease condition of choice.

The present invention also provides kits for producing single-dose or multi-dose administration units of site-specific conjugates and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed conjugates in a conjugated or unconjugated form. In other preferred embodiments, the container(s) comprise a sterile access port (for example the container may be an intravenous solution bag or a vial having a stopper pierceable by a hypodermic injection needle). Such kits will generally contain in a suitable container a pharmaceutically acceptable formulation of the engineered conjugate and, optionally, one or more anti-cancer agents in the same or different containers. The kits may also contain other pharmaceutically acceptable formulations, either for diagnosis or combined therapy. For example, in addition to the antibody or the antigen-binding portion thereof of the invention such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents.

More specifically the kits may have a single container that contains the disclosed the antibody or the antigen-binding portion thereof, with or without additional components, or they may have distinct containers for each desired agent. Where combined therapeutics are provided for conjugation, a single solution may be pre-mixed, either in a molar equivalent combination, or with one component in excess of the other. Alternatively, the conjugates and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous or saline solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody or the antigen-binding portion thereof and any optional components to a patient, e.g., one or more needles, I.V. bags or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained.

Sequence Listing Summary

Appended to the instant application is a sequence listing comprising a number of nucleic acid and amino acid sequences. The following Table A provides a summary of the included sequences.

Four illustrative antibodies as disclosed herein, which are fully human anti-4-1BB monoclonal antibodies, are designated as "2.19.8-u1-3-hIgG1L," "2.19.8-u1-3-hIgG4L," "2.27.16-u1-1-h3gG1L," and "2.27.16-u1-1-hIgG4L," respectively. Antibodies "2.19.8-u1-3-hIgG1L" and "2.19.8-u1-3-hIgG4L" are the same variable regions (including heavy chain variable region and light chain variable regions), and differ from each other in that the constant region of the antibody "2.19.8-u1-3-hIgG1L" is human IgG1 constant region, and the constant region of the antibody "2.19.8-u1-3-hIgG4L" is human gG4 constant region. Similarly, antibodies "2.27.16-u1-1-hIgG1L" and "2.27.16-u1-1-hIgG4L" are the same variable regions (including heavy chain variable region and light chain variable regions), and differ from each other in that the constant region of the antibody "2.27.16-u1-1-hIgG1L" is human IgG1 constant region, and the constant region of the antibody "2.27.16-u1-1-hIgG4L" is human gG4 constant region.

TABLE A

| SEQ ID NO. | Description |
|---|---|
| 1 | CDRH1 of "2.19.8-u1-3-hIgG1L" or "2.19.8-u1-3-hIgG4L" |
| 2 | CDRH2 of "2.19.8-u1-3-hIgG1L" or "2.19.8-u1-3-hIgG4L" |
| 3 | CDRH3 of "2.19.8-u1-3-hIgG1L" or "2.19.8-u1-3-hIgG4L" |
| 4 | CDRL1 of "2.19.8-u1-3-hIgG1L" or "2.19.8-u1-3-hIgG4L" |
| 5 | CDRL2 of "2.19.8-u1-3-hIgG1L" or "2.19.8-u1-3-hIgG4L" |
| 6 | CDRL3 of "2.19.8-u1-3-hIgG1L" or "2.19.8-u1-3-hIgG4L" |
| 7 | CDRH1 of "2.27.16-u1-1-hIgG1L" or "2.27.16-u1-1-hIgG4L" |
| 8 | CDRH2 of "2.27.16-u1-1-hIgG1L" or "2.27.16-u1-1-hIgG4L" |
| 9 | CDRH3 of "2.27.16-u1-1-hIgG1L" or "2.27.16-u1-1-hIgG4L" |

TABLE A-continued

| SEQ ID NO. | Description |
|---|---|
| 10 | CDRL1 of "2.27.16-u1-1-hIgG1L" or "2.27.16-u1-1-hIgG4L" |
| 11 | CDRL2 of "2.27.16-u1-1-hIgG1L" or "2.27.16-u1-1-hIgG4L" |
| 12 | CDRL3 of "2.27.16-u1-1-hIgG1L" or "2.27.16-u1-1-hIgG4L" |
| 13 | VH of "2.19.8-u1-3-hIgG1L" or "2.19.8-u1-3-hIgG4L" |
| 14 | VL of "2.19.8-u1-3-hIgG1L" or "2.19.8-u1-3-hIgG4L" |
| 15 | VH of "2.27.16-u1-1-hIgG1L" or "2.27.16-u1-1-hIgG4L" |
| 16 | VL of "2.27.16-u1-1-hIgG1L" or "2.27.16-u1-1-hIgG4L" |
| 17 | DNA sequence encoding VH of "2.19.8-u1-3-hIgG1L" or "2.19.8-u1-3-hIgG4L" |
| 18 | DNA sequence encoding VL of "2.19.8-u1-3-hIgG1L" or "2.19.8-u1-3-hIgG4L" |
| 19 | DNA sequence encoding VH of "2.27.16-u1-1-hIgG1L" or "2.27.16-u1-1-hIgG4L" |
| 20 | DNA sequence encoding VL of "2.27.16-u1-1-hIgG1L" or "2.27.16-u1-1-hIgG4L" |
| 21 | Amino acid sequence of full-length human 4-1BB |
| 22 | Amino acid sequence of extracellular domain of human 4-1BB |

Specifically, the CDR sequences of the four illustrative antibodies as disclosed herein, which are fully human anti-4-1BB monoclonal antibodies, are shown in Table B, and the amino acid sequences and nucleotide sequences of VH and VL of the four illustrative antibodies are shown in Table C and D, respectively.

TABLE B

Amino acid sequences of CDRs

| Name | Chain | CDR1 | CDR2 | CDR3 |
|---|---|---|---|---|
| "2.19.8-u1-3-hIgG1L" and "2.19.8-u1-3-hIgG4L" | CDRH | SEQ ID NO: 1 GFTFSDYFMS | SEQ ID NO: 2 YISNAGSSKYYAD SVKG | SEQ ID NO: 3 DPYSGSYSGWFD P |
| | CDRL | SEQ ID NO: 4 SGDDLGDKYTS | SEQ ID NO: 5 QDHKRPS | SEQ ID NO: 6 QAWDKGIVV |
| "2.27.16-u1-1-hIgG1L" and "2.27.16-u1-1-hIgG4L" | CDRH | SEQ ID NO: 7 GGSINSQGYYWS | SEQ ID NO: 8 YIYDSGSAYYNPS LER | SEQ ID NO: 9 IVAAGRIDP |
| | CDRL | SEQ ID NO: 10 GGDNIGIKIVH | SEQ ID NO: 11 DDNDRPS | SEQ ID NO: 12 QVWDRRSDHVV |

TABLE C

Amino acid sequences of viable regions

| Name | VH | VL |
|---|---|---|
| "2.19.8-u1-3-hIgG1L" and "2.19.8-u1-3-hIgG4L" | SEQ ID NO: 13 QVQLVESGGGLVKPGGSLRL SCAASGFTFSDYFMSWIRQA PGKGLEWVSYISNAGSSKYY ADSVKGRFTISRDNAKNSLY LQMNSLRAEDTAVYYCVRD PYSGSYSGWFDPWGQGTLV TVSS | SEQ ID NO: 14 SYDLTQPPSVSVSPGQTASITCSG DDLGDKYTSWYQQKPGQSPVLV VYQDHKRPSGIPERFSGSNSGNT ATLTISGTQAMDEADYYCQAWD KGIVVFGGGTKLTVL |

TABLE C-continued

Amino acid sequences of viable regions

| Name | VH | VL |
|---|---|---|
| "2.27.16-u1-1-hIgG1L" and "2.27.16-u1-1-hIgG4L" | SEQ ID NO: 15<br>QEQLQESGPGLVKPSQTLSLT<br>CTVSGGSINSQGYYWSWIRQ<br>HPGKGLEWIGYIYDSGSAYY<br>NPSLERRVAISLDTSKNQFSL<br>NLNSVTVADTAVYYCARIVA<br>AGRIDPWGQGTLVTVSS | SEQ ID NO: 16<br>SYVLTQPPSVSVAPGQTARMTCG<br>GDNIGIKIVHWYQQKAGQAPVL<br>VVYDDNDRPSGIPDRFSGSNSGN<br>TATLTISRVAAGDEADYYCQVW<br>DRRSDHVVFGGGTKLTVL |

TABLE D

Nucleotide sequences of viable regions

| Name | VH | VL |
|---|---|---|
| "2.19.8-u1-3-hIgG1L" and "2.19.8-u1-3-hIgG4L" | SEQ ID NO: 17<br>CAGGTGCAACTGGTGGAGT<br>CTGGGGGAGGCTTGGTCAA<br>GCCTGGAGGGTCCCTGAGA<br>CTGTCCTGTGCAGCCTCTG<br>GATTCACCTTCAGTGACTAC<br>TTCATGAGCTGGATCCGCC<br>AGGCTCCAGGGAAGGGGC<br>TGGAATGGGTTTCATACATT<br>AGTAATGCCGGTAGTTCCA<br>AATATTATGCAGACTCCGTG<br>AAGGGCCGATTCACCATCT<br>CCAGGGACAACGCCAAGA<br>ACTCACTGTATCTGCAAATG<br>AACAGTCTGAGAGCCGAG<br>GACACGGCCGTGTATTACT<br>GTGTGAGAGATCCTTATAGT<br>GGGAGTTACTCCGGGTGGT<br>TCGACCCCTGGGGCCAGGG<br>AACCCTGGTCACCGTCTCC<br>TCA | SEQ ID NO: 18<br>TCCTATGACCTGACTCAGCCAC<br>CCTCAGTGTCCGTGTCCCCAGG<br>ACAGACAGCCAGCATCACCTGT<br>TCTGGAGATGATTTGGGAGATA<br>AATATACTAGCTGGTATCAGCA<br>GAAGCCGGGCCAGTCCCCTGTA<br>TTGGTCGTCTATCAAGATCACA<br>AGCGGCCCTCAGGGATCCCTGA<br>GCGATTCTCTGGCTCCAATTCT<br>GGGAACACAGCCACTCTGACC<br>ATCAGCGGGACCCAGGCTATGG<br>ATGAGGCTGACTATTACTGTCA<br>GGCGTGGGACAAGGGCATTGT<br>GGTATTCGGCGGAGGGACCAA<br>ACTGACCGTCCTA |
| "2.27.16-u1-1-hIgG4L" and "2.27.16-u1-1-hIgG1L" | SEQ ID NO: 19<br>CAGGAGCAGCTGCAGGAG<br>TCGGGCCCAGGACTGGTGA<br>AGCCTTCACAGACCTTGTC<br>CCTCACCTGCACTGTCTCT<br>GGTGGCTCCATCAACAGTC<br>AGGGTTACTACTGGAGCTG<br>GATCCGCCAGCACCCAGGG<br>AAGGGCCTGGAGTGGATTG<br>GGTACATCTATGACAGTGG<br>AAGTGCCTACTACAATCCG<br>TCCCTCGAGAGGCGAGTTG<br>CCATATCATTAGACACGTCT<br>AAGAACCAGTTCTCCCTGA<br>ACCTGAACTCTGTGACTGT<br>CGCGGACACGGCCGTTTAT<br>TACTGCGCGAGGATAGTAG<br>CAGCTGGTCGGATCGACCC<br>CTGGGGCCAGGGAACCCTG<br>GTCACCGTCTCCTCA | SEQ ID NO: 20<br>TCCTATGTCCTGACTCAGCCAC<br>CCTCGGTGTCAGTGGCCCCCGG<br>ACAGACGGCCAGGATGACCTG<br>TGGGGGAGACAACATTGGAATT<br>AAAATTGTGCACTGGTACCAGC<br>AGAAGGCAGGCCAGGCCCCTG<br>TGTTGGTCGTCTATGATGATAAT<br>GACCGGCCCTCAGGGATCCCTG<br>ACCGATTCTCTGGCTCCAACTC<br>TGGGAACACGGCCACCCTGAC<br>CATCAGCAGGGTCGCAGCCGG<br>GGATGAGGCCGACTACTACTGT<br>CAGGTGTGGGATAGGAGGAGT<br>GATCATGTGGTTTTCGGCGGAG<br>GGACCAAGTTGACCGTCCTA |

EXAMPLES

The present invention, thus generally described, will be understood more readily by reference to the following Examples, which are provided by way of illustration and are not intended to be limiting of the instant invention. The Examples are not intended to represent that the experiments below are all or the only experiments performed.

Example 1

Preparation of Materials 1.1 Immunogen Generation

Nucleic acid encoding full-length human, mouse and cynomolgus 4-1BB or 4-1BB ECD (extracellular domain, ECD) was synthesized by Sangon Biotech. 4-1BB gene fragments were amplified from the synthesized nucleic acid and inserted into the expression vector pcDNA3.3 (ThermoFisher). The inserted 4-1BB gene fragment was further confirmed by DNA sequencing. Fusion proteins containing human and mouse 4-1BB ECD with various tags, including human Fc, cynomolgus Fc, mouse Fc and His tags, were obtained by transfection of human 4-1BB gene into 293F cells (ThermoFisher). The cells were cultured in a FreeStyle 293 Expression Medium (ThermoFisher) at 37° C., 5% $CO_2$. After 5 days of culture, supernatants harvested from the culture of transiently transfected cells were used for protein purification. The fusion proteins were purified by nickel, protein A and/or SEC column, and quantitated for immunization, screening and characterization.

1.2 Production of Benchmark Antibodies

Gene sequences of anti-human 4-1BB benchmark antibodies (BMK3 and BMK4) were synthesized based on the information disclosed in patent applications U.S. Pat. No. 7,288,638B2 and US 20130078240A1 (BMK3 was referred to as "20H4.9-IgG1,4" in U.S. Pat. No. 7,288,638B2) and (BMK4 was referred to as "PF05082566" in US 20130078240A1), respectively. The synthesized gene sequences were incorporated into plasmids pcDNA3.3, as described in above section 1. The plasmids were transiently transfected into 293F cells. The cells were cultured in the same way as described in section 1. After 5 days of culture, supernatants harvested from the culture of transiently transfected cells were used for protein purification. The benchmark antibodies were purified from the supernatants.

1.3 Establishment of Stable Cell Lines

Human, mouse and cynomolgus 4-1BB transfectant cell lines were generated. Briefly, Flp-In-293, Flp-In-CHO or 293F cells were transfected with pcDNA3.3 expression vector containing full-length of human, mouse and cynomolgus 4-1BB using Lipofectamine 2000 transfection kit according to manufacturer's protocol, respectively. At 48-72 hours post transfection, the transfected cells were cultured in medium containing Blasticidin for selection and tested for 4-1BB expression. Human 4-1BB-expressing cell lines, cynomolgus monkey 4-1BB-expressing cell lines, and mouse 4-1BB expressing cell lines were obtained by limited dilution and scaled up to large volumes. The established monoclonal cell lines were then maintained in medium containing proper dose of Blasticidin.

Example 2

Antibody Hybridoma Generation 2.1 Immunization and Cell Fusion

OMT rats (transgenic rats having recombinant immunoglobulin loci, as described and produced in U.S. Pat. No. 8,907,157 B2), 6-8 weeks of age, were immunized with 20 μg of human 4-1BB ECD protein in TiterMax subcutaneously, and boosted every week with human or mouse 4-1BB ECD protein in Alum-Phos and TiterMax, alternately. Animals were bled monthly for serum collection and anti-4-1BB antibody titers were measured by ELISA. Once the antibody titer reached sufficiently high, rats were given a final boost with 35 μg of human 4-1BB ECD protein in DPBS without adjuvant. The cell fusion was performed as following: B lymphocytes were isolated from lymph nodes dissected from immunized animals under sterile condition. The isolated B cells were then mixed with myeloma cell SP2/0 at the ratio of 1:1. Electro cell fusion was performed using BTX 2000 Electro cell manipulator. The cells were then seeded in 96-well plates and cultured at 37° C., 5% $CO_2$ until ready for screening.

2.2 Primary and Confirmatory Screening of Hybridoma Supernatants

ELISA assay was used as the first screening method to select the supernatant samples containing antibodies that bind to human and cynomolgus monkey 4-1BB proteins. Briefly, plates (Nunc) were coated with soluble protein of human or cynomolgus 4-1BB extracellular domain overnight at 4° C. After blocking and washing, the hybridoma supernatants were transferred to the coated plates and incubated at room temperature for 1 h. The plates were then washed and subsequently incubated with secondary antibody goat anti-rat IgG HRP (Bethyl) for 45 min. After washing, TMB substrate was added and the color reaction was stopped by 2M HCl. The absorbance at 450 nm was read using a microplate reader (Molecular Device).

In order to confirm the binding of 4-1BB antibodies on native 4-1BB molecules expressed on cell membrane, flow cytometry analysis was performed using 4-1BB transfected CHO-K1 cell line. CHO-K1 cells expressing human 4-1BB were transferred into 96-well U-bottom plates (BD). The hybridoma supernatants selected according to primary screening results were then transferred to the plates and incubated for 1 h at 4° C. After washing, the secondary antibody goat anti-rat IgG HRP (Bethyl) was added and incubated with cells at 4° C. in the dark for 1 h. The cells were then washed and resuspended in PBS before being analyzed by flow cytometer (BD). The binding of antibodies to parental CHO-K1 cell line was performed in parallel as negative controls.

2.3 Hybridoma Sub-Cloning:

Once specific binding was verified through primary and confirmatory screening, the positive hybridoma cell lines were sub-cloned to get monoclonal anti-h4-1BB antibodies. Briefly, for each hybridoma cell line, cells were counted and serially diluted into Dulbecco's Modified Eagle's Medium. The cell suspension was plated into 96-well plates. Plates were cultured at 37° C., 5% $CO_2$, until they were ready to be checked by ELISA. The exhausted supernatant (ESN) of selected single clones were collected for purification.

Example 3

Hybridoma Sequencing and Fully Human Antibody Molecules Construction and Purification 3.1 Hybridoma Sequencing Total RNA was extracted from hybridoma cells by using RNeasy Plus Mini Kit (Qiagen) and first strand cDNA was prepared as shown in Table 1 and Table 2. Antibody VH and VL genes were amplified from cDNA as shown in Table 3 and Table 4 by using 3'-constant region degenerated primer and 5'-degenerated primer sets, which are complementary to the upstream signal sequence-coding region of Ig variable sequences. Reagent information including the manufactures is shown in Table 5.

The PCR product (10 μL) was ligated into pMD18-T vector and 10 μL of the ligation product was transformed into Top10 competent cells. Transformed cells were plated on 2-YT+Cab plates and incubated overnight at 37° C. Positive clones were randomly picked for sequencing at Shanghai Biosune Biotech Co., Ltd.

TABLE 1

| cDNA amplification reaction (20 μL) | |
| --- | --- |
| Component | Amount |
| Up to 5 μg total RNA | 5 μL |
| Primer (50 μM oligo(dT)$_{20}$/50 ng/μL random hexamers) | 1 μL/1 μL |
| Annealing Buffer | 1 μL |
| RNase/DNase-free water | to 8 μL |
| 65° C. for 5 min, then immediately place on ice for at least 1 minute | |
| 2× First-Strand Reaction Mix | 10 μL |
| SuperScript ™ III/RNaseOUT ™ Enzyme Mix | 2 μL |

TABLE 2

| cDNA amplification reaction condition | | | | |
| --- | --- | --- | --- | --- |
| | Step 1 | Step 2 | Step 3 | Step 4 |
| Temperature (° C.) | 25 | 50 | 85 | 4 |
| Time | 10 min | 50 min | 5 min | ∞ |

TABLE 3

| PCR Reaction system (50 μL) | |
| --- | --- |
| Component | Amount |
| cDNA | 2.0 μL |
| Premix Ex Taq | 25 μL |
| 5'-degenerated primer sets (10 pM) | 2.5 μL |
| 3'-constant region degenerated primer (10 pM) | 1 μL |
| ddH$_2$O | 19.5 μL |

TABLE 4

| PCR Reaction condition | | | | | |
| --- | --- | --- | --- | --- | --- |
| | Step 1 | Step 2 | Step 3 | Step 4 | Step 5 |
| Temperature (° C.) | 95 | 94 | 58 | 72 | 72 |
| Time | 4 min | 45 sec | 45 sec | 1 min | 10 min |
| Cycles | NA | | 30 | NA | NA |

TABLE 5

| Reagent information | |
| --- | --- |
| Reagent | Manufacturers |
| RNeasy Plus Mini Kit | QIAGEN |
| SuperScript III First-Strand Synthesis SuperMix | Invitrogen |
| Premix Ex Taq hot start | TaKaRa |
| DNA Gel Extraction Kit | Axygen |
| pMD 18-T vector | TaKaRa |

Upon sequencing, the sequences of illustrative antibodies were obtained, and the sequence information was provided in above Table A.

3.2 Fully Human Antibody Molecule Construction and Purification

VH and VL genes were re-amplified with cloning primers containing appropriate restriction sites and cloned into WuXi Biologics' proprietary expression vector pcDNA3.4. Expi-293F cells were transiently transfected with the vector for antibody expression. The culture supernatant containing antibodies was harvested and purified using Protein A chromatography.

Example 4

Antibody Characterization 4.1 Full Kinetic Binding Affinity Test by Surface Plasmon Resonance (SPR)

Antibodies were characterized for affinity and binding kinetics to human, cynomolgus and mouse 4-1BB by SPR assay using Biacore T200 (GE). Protein G was pre-immobilized to a sensor chip (CM5), and anti-4-1BB antibodies were captured when injected to the chip. Various concentrations of human 4-1BB and running buffer were flowed through the sensor chip for an association phase, and followed by dissociation. The association and dissociation curve was analyzed using Biacore T200 Evaluation software Version 2.0.

Experimental results are shown in Table 6 and Table 7 below.

TABLE 6

Full kinetics binding affinity of 4-1BB antibodies against recombinant human 4-1BB protein using surface plasmon resonance.

| Analyte | Ligand | ka (1/Ms) | kd (1/s) | $K_D$ (M) |
| --- | --- | --- | --- | --- |
| hPro1.ECD.His* | 2.19.8-u1-3-hIgG1L | $2.52 \times 10^6$ | $6.48 \times 10^{-5}$ | $2.57 \times 10^{-11}$ |
| | 2.19.8-u1-3-hIgG4L | $2.11 \times 10^6$ | $3.74 \times 10^{-5}$ | $1.77 \times 10^{-11}$ |
| | 2.27.16-u1-1-hIgG1L | $2.87 \times 10^5$ | $5.11 \times 10^{-5}$ | $1.78 \times 10^{-10}$ |
| | 2.27.16-u1-1-hIgG4L | $2.45 \times 10^5$ | $3.92 \times 10^{-5}$ | $1.60 \times 10^{-10}$ |
| | BMK3.hIgG1(BMS) | $1.06 \times 10^6$ | $2.53 \times 10^{-3}$ | $2.39 \times 10^{-9}$ |
| | BMK4.hIgG1L(Pfizer) | $8.15 \times 10^5$ | $2.15 \times 10^{-2}$ | $2.64 \times 10^{-8}$ |

*human 4-1BB extracellular domain, His tag

As shown in Table 6, the affinities of the illustrative antibodies (including 2.19.8-u1-3-hIgG1L, 2.19.8-u1-3-hIgG4L, 2.27.16-u1-1-hIgG1L and 2.27.16-u1-1-hIgG4L) against 4-1BB for recombinant human 4-1BB are from $1.77 \times 10^{-11}$ M to $1.78 \times 10^{-10}$ M.

TABLE 7

Full kinetics binding affinity of 4-1BB antibodies against recombinant cynomolgus 4-1BB protein using surface plasmon resonance.

| Analyte | Ligand | ka (1/Ms) | kd (1/s) | $K_D$ (M) |
|---|---|---|---|---|
| cynoPro1.ECD.His* (ACRO-41B-C52H4) | 2.19.8-u1-3-hIgG1L | $1.81 \times 10^6$ | $2.96 \times 10^{-5}$ | $1.64 \times 10^{-11}$ |
| | 2.19.8-u1-3-hIgG4L | $1.86 \times 10^6$ | $2.93 \times 10^{-5}$ | $1.58 \times 10^{-11}$ |
| | 2.27.16-u1-1-hIgG1L | $2.17 \times 10^5$ | $3.07 \times 10^{-5}$ | $1.42 \times 10^{-10}$ |
| | 2.27.16-u1-1-hIgG4L | $2.30 \times 10^5$ | $1.01 \times 10^{-4}$ | $4.39 \times 10^{-10}$ |
| | BMK4.hIgG2L(Pfizer) | $1.09 \times 10^6$ | $1.74 \times 10^{-2}$ | $1.60 \times 10^{-8}$ |

*cynomolgus 4-1BB extracellular domain, His tag

As shown in Table 7, the affinities of the illustrative antibodies (including 2.19.8-u1-3-hIgG1L, 2.19.8-u1-3-hIgG4L, 2.27.16-u1-1-hIgG1L and 2.27.16-u1-1-hIgG4L) against 4-1BB for recombinant cynomolgus 4-1BB are from $1.58 \times 10^{-11}$ M to $4.39 \times 10^{-10}$ M.

TABLE 8

Full kinetics binding affinity of 4-1BB antibodies against recombinant mouse 4-1BB protein using surface plasmon resonance.

| Analyte | Ligand | ka (1/Ms) | kd (1/s) | $K_D$ (M) |
|---|---|---|---|---|
| mPro1.ECD.His* | 2.19.8-u1-3-hIgG1L | $3.73 \times 10^7$ | $9.75 \times 10^{-1}$ | $2.61 \times 10^{-8}$ |
| | 2.19.8-u1-3-hIgG4L | $1.17 \times 10^7$ | $2.15 \times 10^{-1}$ | $1.84 \times 10^{-8}$ |
| | 2.27.16-u1-1-hIgG1L | $1.58 \times 10^5$ | $1.34 \times 10^{-3}$ | $8.49 \times 10^{-9}$ |
| | 2.27.16-u1-1-hIgG4L | $2.17 \times 10^5$ | $1.36 \times 10^{-3}$ | $6.27 \times 10^{-9}$ |

*mouse 4-1BB extracellular domain, His tag

As shown in Table 8, the affinities of the illustrative antibodies (including 2.19.8-u1-3-hIgG1L, 2.19.8-u1-3-hIgG4L, 2.27.16-u1-1-hIgG1L and 2.27.16-u1-1-hIgG4L) against 4-1BB for recombinant mouse 4-1BB are from $6.27 \times 10^{-9}$ to $2.61 \times 10^{-8}$ M.

4.2 Binding of Antibodies to Cell Surface 4-1BB Molecules by Flow Cytometry.

Human 4-1BB-expressing CHO-K1 cells were transferred into 96-well U-bottom plates at a density of $1 \times 10^5$ cells/well. Testing antibodies (including the illustrative antibodies of the invention, and BMK3 and BMK4) were serially diluted and incubated with cells at 4° C. for 1 h. After washing, the secondary antibody, PE labeled Goat anti-human IgG Fc Fragment (Jackson ImmunoResearch), was applied and incubated with cells at 4° C. in the dark for 1 h. The cells were then washed and re-suspended in PBS and then analyzed by a flow cytometer (BD).

Figure 1:
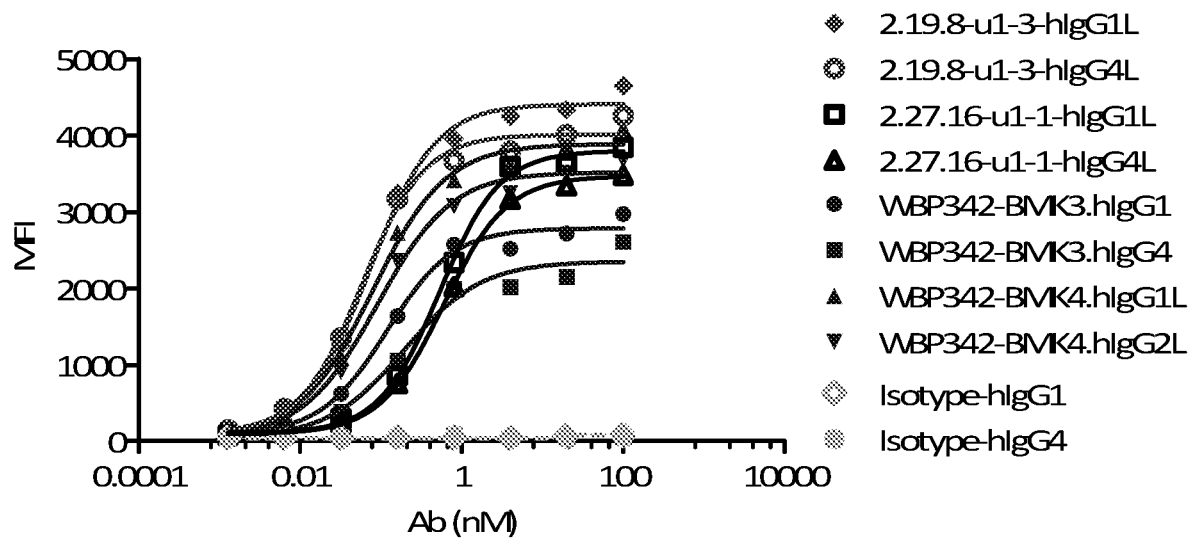
FIG. 1 shows the binding of anti-human 4-1BB antibodies to human 4-1BB expressing CHO-K1 cells by Flow Cytometry, expressed by MFI (Median Fluorescence Intensity) and measured by BD FACSCanto II, as described in Example 4.2.

The data for binding of anti-human 4-1BB antibodies to human 4-1BB expressing CHO-K1 cells by Flow Cytometry are shown in FIG. 1. The data demonstrate that the illustrative antibodies show well binding efficiency to human 4-1BB expressing CHO-K1 cells.

4.3 Binding of Antibodies to Activated Human T Cells by Flow Cytometry.

Human T cells were isolated from human PBMCs using Human T Cell Enrichment Kit (StemCell) according to the manufacturer's protocol. Separated human T cells were stimulated by PMA and inomycin for 48 hours. Cells were transferred into 96-well U-bottom plates at a density of $1 \times 10^5$ cells/well. Serially diluted antibodies were added and incubated with cells at 4° C. for 1 h. After washing, the secondary antibody, PE labeled Goat anti-human IgG Fc Fragment (Jackson ImmunoResearch), was applied and incubated with cells at 4° C. in the dark for 1 h. The cells were then washed and re-suspended in PBS and then analyzed by a flow cytometer (BD).

Figure 2:
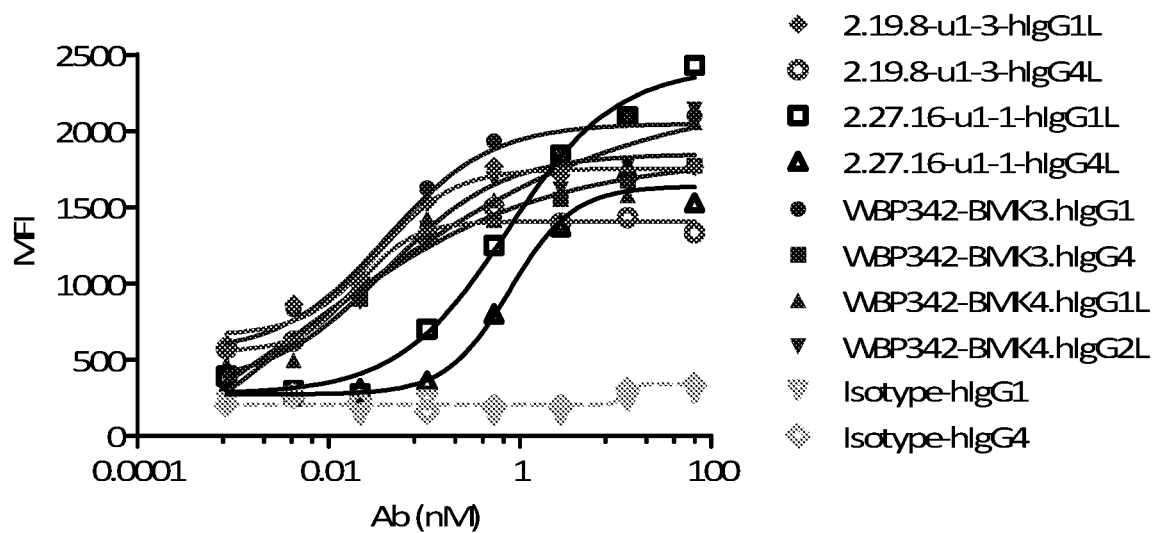
FIG. 2 shows the binding of anti-human 4-1BB antibodies to activated human T cells by Flow Cytometry, as described in Example 4.3.

The data for binding of anti-4-1BB antibodies to activated human T cells by Flow Cytometry are shown in FIG. 2. The data show that the illustrative antibodies bind to activated human T cells in a dose-dependent manner.

4.4 Orthologue (Cross-Species) Test 4.4.1 Cross-Reactivity to Cynomolgus 4-1BB was Measured by Flow Cytometry.

Cynomolgus 4-1BB-expressing Flp-CHO cells were transferred into 96-well U-bottom plates at a density of $1 \times 10^5$ cells/well. Testing antibodies were serially diluted in PBS containing 1% BSA, and incubated with cells at 4° C. for 1 h. After washing, the secondary antibody, PE labeled Goat anti-human IgG Fc Fragment (Jackson ImmunoResearch), was applied and incubated with cells at 4° C. in the dark for 1 h. The cells were then washed and resuspended in PBS and then analyzed by flow cytometer (BD).

Figure 3:
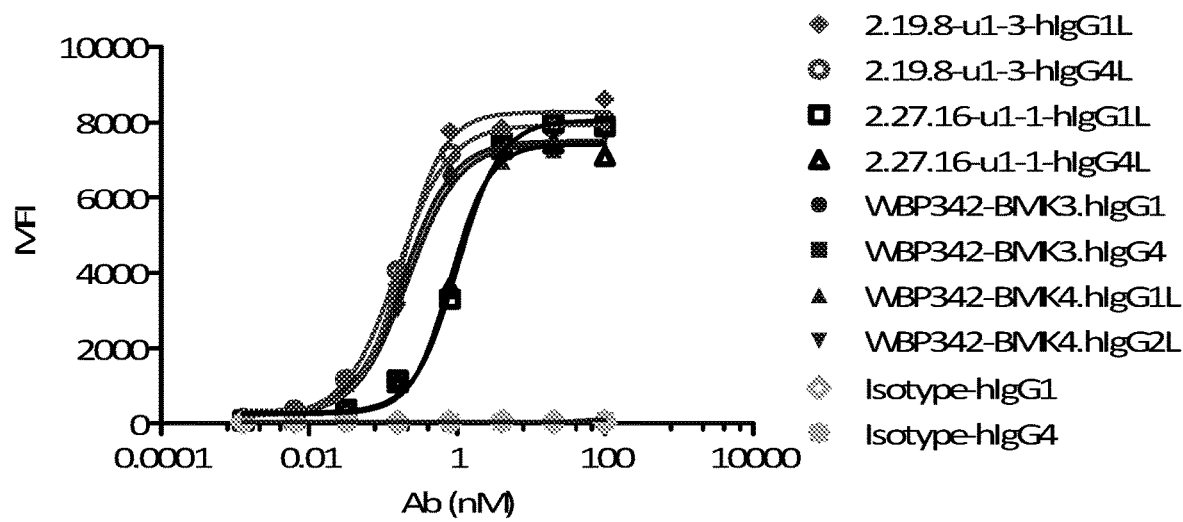
FIG. 3 shows the cross-species binding of anti-4-1BB antibodies to cynomolgus 4-1BB expressing CHO-K1 cells by Flow Cytometry, as described in Example 4.4.1.

As demonstrated in FIG. 3, the illustrative antibodies have cross binding to cynomolgus 4-1BB expressing CHO-K1 cells.

4.4.2 Cross-Reactivity to Murine 4-1BB was Measured by Flow Cytometry.

Murine 4-1BB-expressing CHO-K1 cells were transferred into 96-well U-bottom plates at a density of $1 \times 10^5$ cells/well. Testing antibodies were serially diluted in PBS containing 1% BSA, and incubated with cells at 4° C. for 1 h. After washing, the secondary antibody, PE labeled Goat anti-human IgG Fc Fragment (Jackson ImmunoResearch), was applied and incubated with cells at 4° C. in the dark for 1 h. The cells were then washed and resuspended in PBS and then analyzed by flow cytometer (BD).

Figure 4:
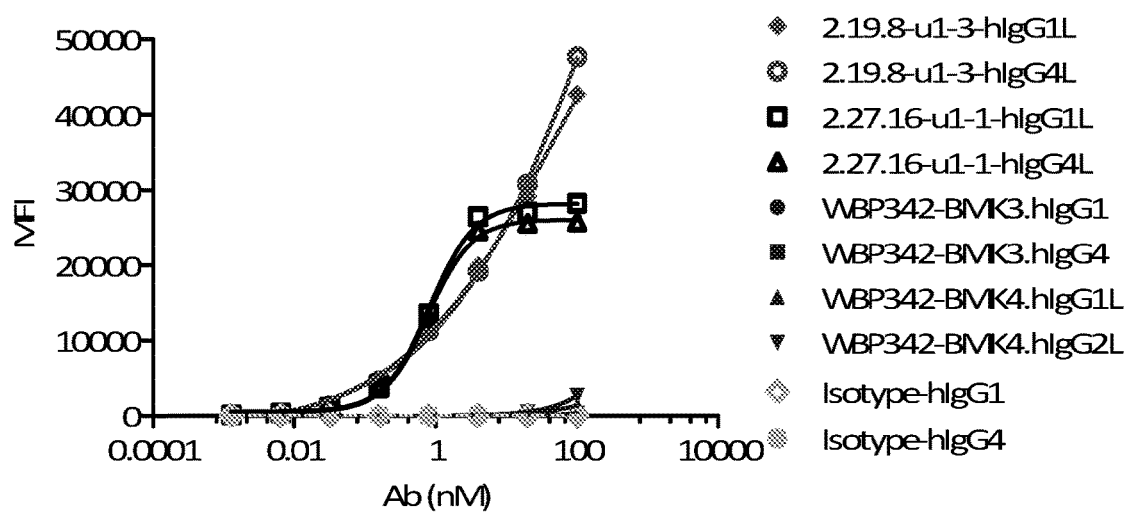
FIG. 4 shows the cross-species binding of anti-4-1BB antibodies to murine 4-1BB expressing CHO-K1 cells by Flow Cytometry, as described in Example 4.4.2.

As demonstrated in FIG. 4, the illustrative antibodies have cross-reactive binding to mouse 4-1BB expressing CHO-K1 cells.

4.5 Homologue (Cross-Family) Test

Cross-reactivity to TNFR family members OX40, CD40 and GITR were determined by ELISA. Plates (Nunc) were coated with OX40, CD40 or GITR overnight at 4° C. After blocking and washing, anti-4-1BB antibodies were added to the plates and incubated at room temperature for 1 h. The plates were then washed and subsequently incubated with secondary antibody, HRP Conjugated Goat anti-human IgG Fc Fragment antibody (Bethyl), for 45 min. After washing, TMB substrate was added and the color reaction was stopped by 2M HCl. The absorbance at 450 and 540 nm were read using a microplate reader (Molecular Device).

Figure 10:
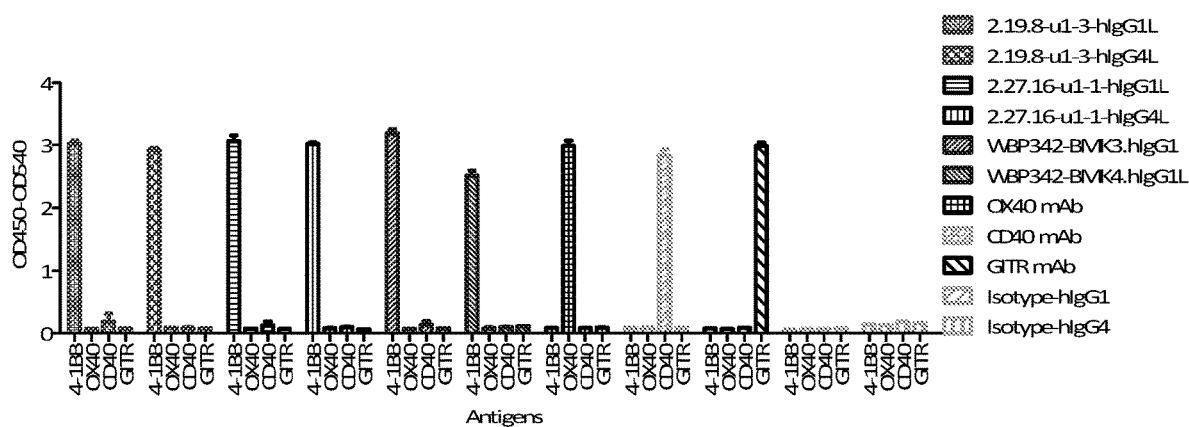
FIG. 10 shows the results of cross family binding test of anti-4-1BB antibodies to other TNFR family members by ELISA, as described in Example 4.5.

Results on cross family binding test of anti-4-1BB antibodies to other TNFR family members by ELISA are shown in FIG. 10. The result demonstrates that 4-1BB antibodies specifically bind to 4-1BB, and do not bind to other family members OX40, CD40 and GITR.

4.6 Epitope Binning Test Against BMK Antibodies

Plates were pre-coated with human 4-1BB protein at 4° C. overnight. After blocking, various concentrations of testing antibodies were pre-mixed with biotinylated BMK antibodies and added to the plates. The plates were incubated at ambient temperature for 1 hour. The binding of the BMK antibodies to human 4-1BB was detected by streptavidin-HRP. The color was developed by dispensing TMB substrate, and then stopped by 2N HCl. The absorbance was read at 450 nM and 540 nM using a microplate spectrophotometer. Experimental Data are shown in FIG. 8 and FIG. 9.

Figure 8:
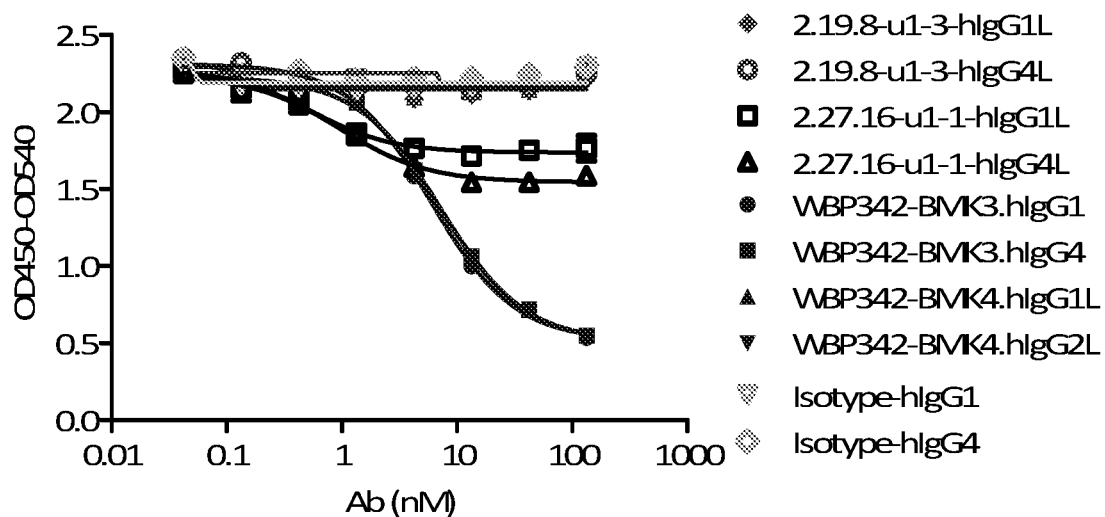
FIG. 8 shows the results of epitope binning test against BMK3 by ELISA, as described in Example 4.6.

The data in FIG. 8 show that the illustrative antibodies 2.27.16-u1-1-hIgG1L and 2.27.16-u1-1-hIgG4L partially competed with BMK3 on binding to human 4-1BB, but the other illustrative antibodies 2.19.8-u1-3-hIgG1L and 2.19.8-u1-3-hIgG4L do not compete with BMK3 on binding to human 4-1BB.

Figure 9:
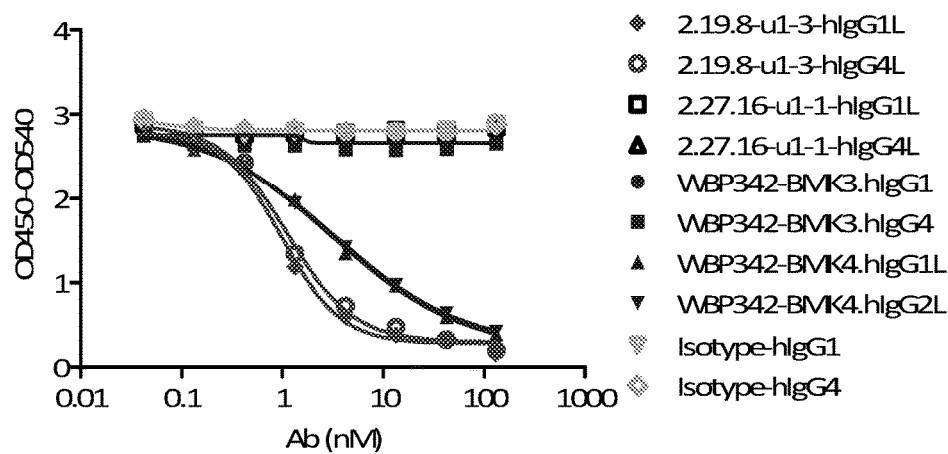
FIG. 9 shows the results of epitope binning test against BMK4 by ELISA, as described in Example 4.6.

The data in FIG. 9 show that the illustrative antibodies 2.19.8-u1-3-hIgG1L and 2.19.8-u1-3-hIgG4L competed with BMK4 on binding to human 4-1BB, but the other illustrative antibodies 2.27.16-u1-1-hIgG1L and 2.27.16-u1-1-hIgG4L do not compete with BMK4 on binding to human 4-1BB.

4.7 Ligand Competition Assay by Flow Cytometry

Human 4-1BB-expressing CHO-K1 cells were transferred into 96-well U-bottom plates at a density of $1\times10^5$ cells/well. Serial dilutions of testing antibodies were premixed with constant concentration of human 4-1BBL-His (BioLegend), and then added to the cells and incubated for 1 hour at 4° C. After washing, anti-His-biotin (GenScript) diluted in PBS was added and incubated with cells at 4° C. for 45 minutes. Cells were washed twice and PE-labeled streptavidin (eBioscience) was used to detect the binding of 4-1BBL onto the cells. MFI of the cells was measured by a flow cytometer and analyzed by FlowJo.

Figure 7:
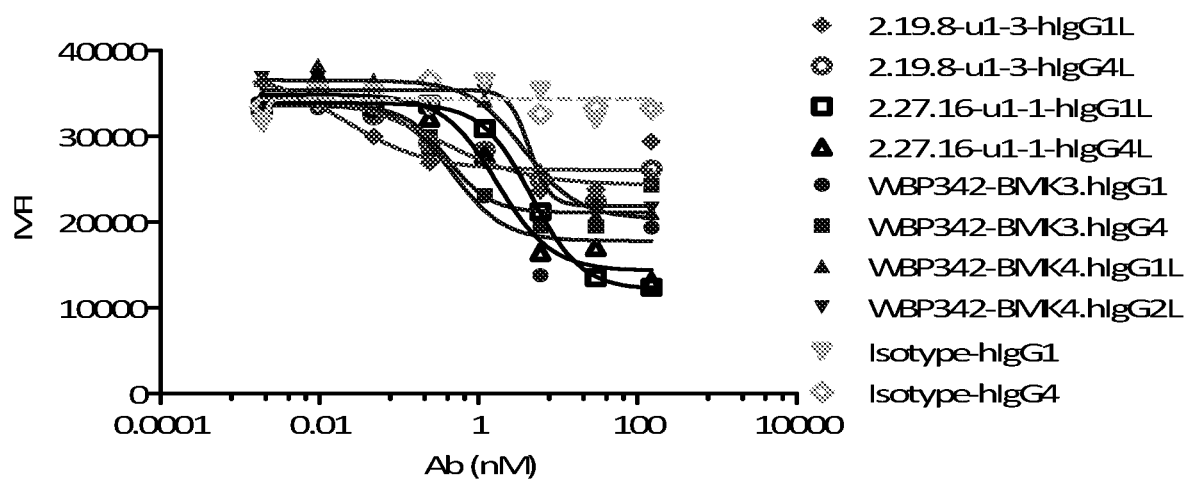
FIG. 7 shows the results of ligand competition test of anti-4-1BB antibodies on engineered CHO-K1 cells by Flow Cytometry, as described in Example 4.7.

The data in FIG. 7 show that the illustrative antibodies 2.27.16-u1-1-hIgG1L and 2.27.16-u1-1-hIgG4L blocked the binding of human 4-1BB ligand (4-1BBL) to human 4-1BB in a similar way as BMK4 (Pfizer), but the illustrative antibodies 2.19.8-u1-3-hIgG1L and 2.19.8-u1-3-hIgG4L partially inhibited the binding of 4-1BBL to 4-1BB in a similar pattern as BMK3 (BMS).

4.8 Reporter Gene Assay for 4-1BB Signaling

CHO-K1 cells expressing human 4-1BB along with stably integrated NF-κB luciferase reporter gene were prepared. The cells were harvested, washed and resuspended in F12K complete medium before adding to a 96-well plate. Serially diluted testing antibodies were added to the cells in the presence of corresponding cross-linking antibodies or CD32 expressing CHO-K1 cells. The plates were incubated for 5 hours at 37° C. After incubation, reconstituted luciferase substrate (Promega) was added and the luciferase intensity was measured by a microplate reader (Molecular Device).

Figure 5:
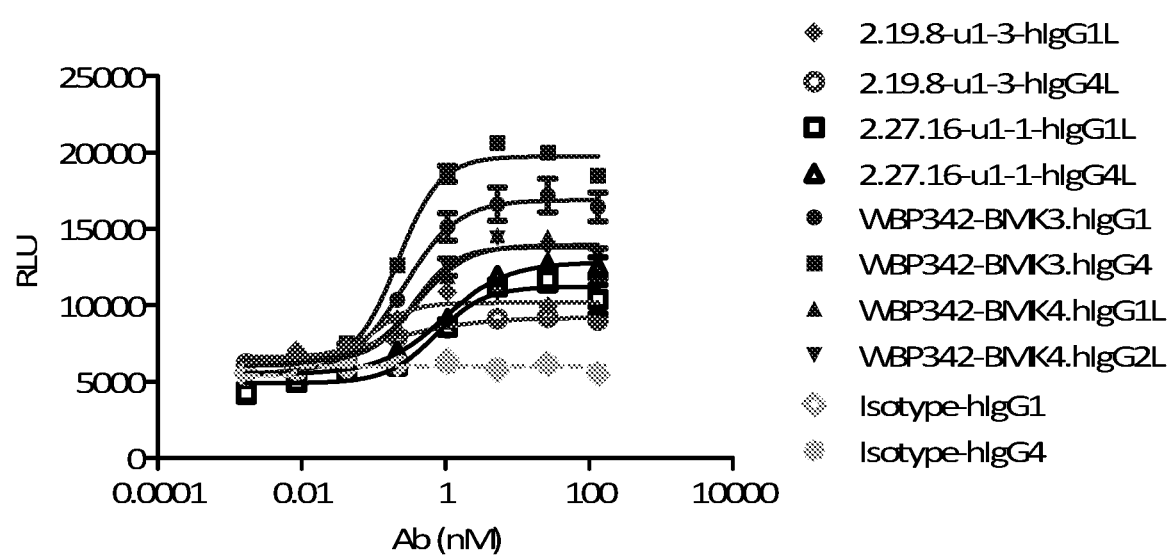
FIG. 5 shows the agonistic effect of anti-4-1BB antibodies with cross-linker by reporter gene assay (RGA), expressed by relative luciferase units (RLU), as described in Example 4.8.

As shown in FIG. 5, the results indicate that the illustrative anti-4-1BB antibodies of the invention showed agonistic effect on 4-1BB signaling and activated the downstream NF-κB pathway.

Figure 6:
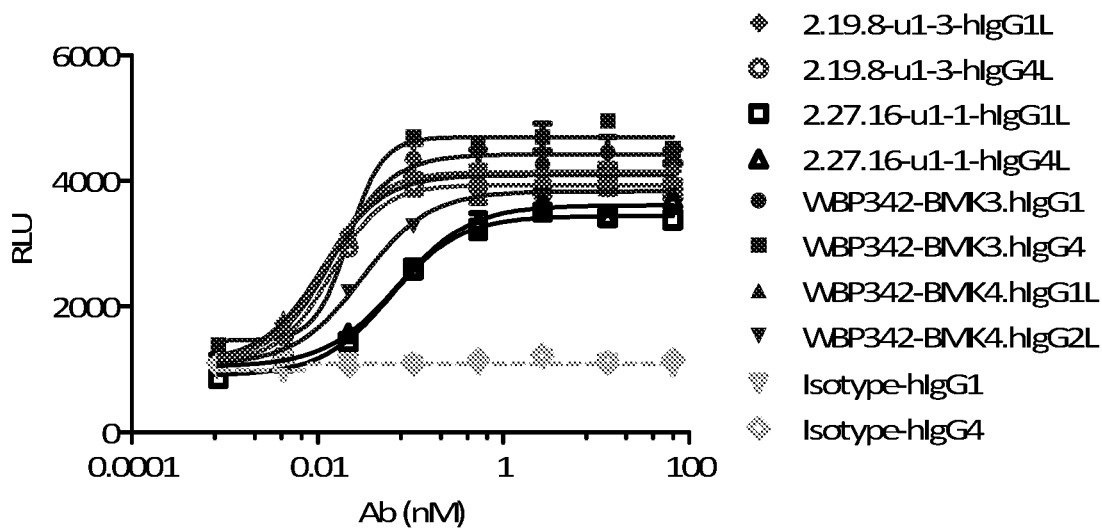
FIG. 6 shows the agonistic effect of anti-4-1BB antibodies with CD32 expressing cells (FIG. 6A) and without CD32 expressing cells (FIG. 6B) by RGA, expressed by RLU, as described in Example 4.8.
Figure 6:
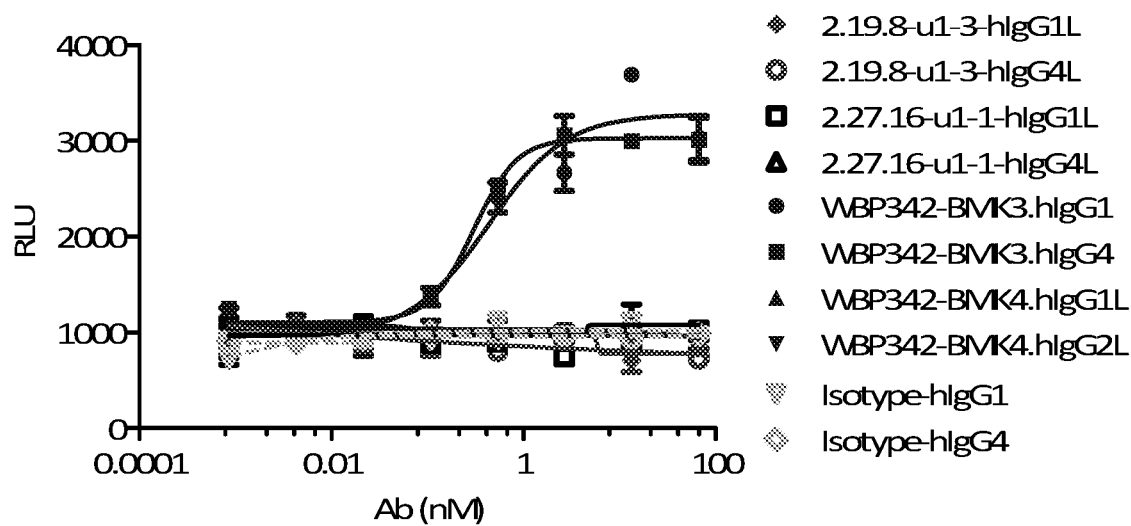

Further, the results in FIG. 6 show that, the anti-4-1BB antibodies of the invention (including 2.19.8-u1-3-hIgG1L, 2.19.8-u1-3-hIgG4L, 2.27.16-u1-1-hIgG1L and 2.27.16-u1-1-hIgG4L) show agonistic effect on 4-1BB signaling with CD32 expressing cells (FIG. 6A), while the antibodies do not show any effect in the absence of CD32 expressing cells except for BMK3 (FIG. 6B).

4.9 Human T Cell In-Vitro Co-Stimulation Assay

Human CD4+ and CD8+ T cells were isolated from human PBMCs using Human CD4+ and CD8+ T Cell Enrichment Kit (StemCell) according to the manufacturer's protocol. The cells were resuspended in complete RPMI 1640 medium.

Effects of anti-4-1BB antibodies on human $CD4^+$ and $CD8^+$ T cells: Briefly, non-tissue culture treated flat-bottom 96-well plates were pre-coated with mouse anti-human CD3 antibody and serial dilutions of anti-4-1BB antibodies. The plates were incubated overnight at 4° C., then washed with complete RPMI 1640 medium to remove unbound antibodies. Freshly isolated human CD4+ or CD8+ T cells were added to each well respectively. The plates were incubated at 37° C., 5% $CO_2$ for 3 days and then supernatants were harvested for IFNγ measurement by ELISA. The cell pellets were harvested to measure T cell proliferation by [$^3$H]-thymidine incorporation. The results on co-stimulation assay are shown in FIGS. 11-14.

Figure 11:
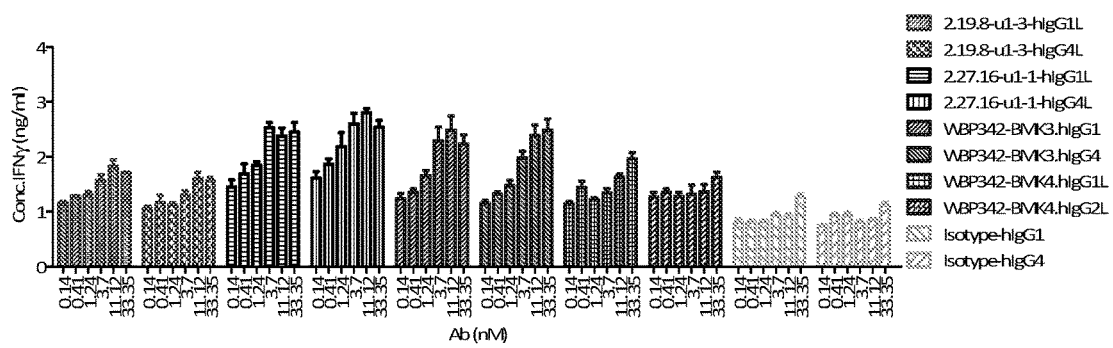
FIG. 11 shows the effect of anti-4-1BB antibodies on IFN-7 secretion in human $CD4^+$ T cell co-stimulation assay, as described in Example 4.9.
Figure 12:
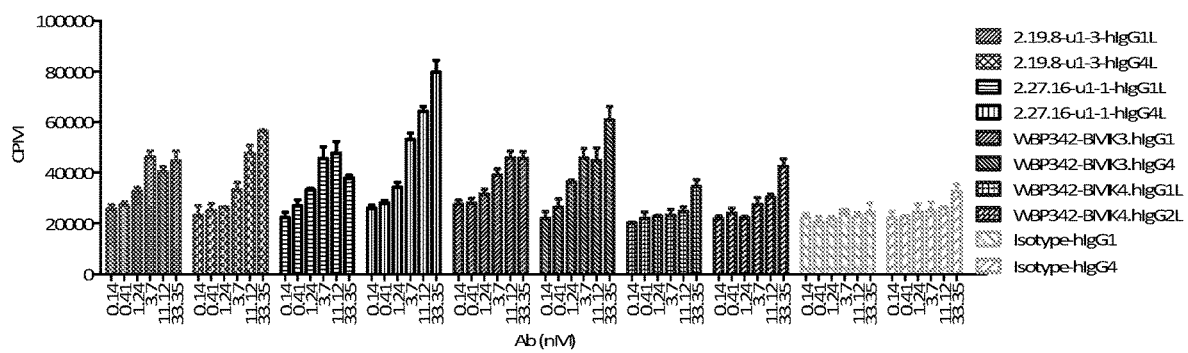
FIG. 12 shows the effect of anti-4-1BB antibodies on cell proliferation in human $CD4^+$ T cell co-stimulation assay, as assessed by [$^3$H] thymidine incorporation and expressed by CPM (counts per minute), as described in Example 4.9.

As shown in FIG. 11, anti-4-1BB antibodies of the invention increase IFN-7 secretion of human $CD4^+$ T cells in a dose-dependent manner. Further, as shown in FIG. 12, the anti-4-1BB antibodies of the invention promote proliferation of $CD4^+$ T cell in a dose-dependent manner.

Figure 13:
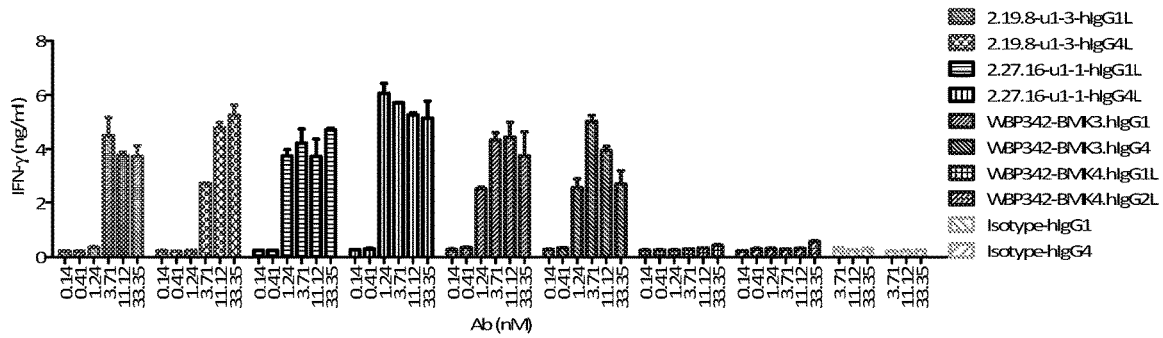
FIG. 13 shows the effect of anti-4-1BB antibodies on IFN-7 production in human $CD8^+$ T cell co-stimulation assay, as described in Example 4.9.
Figure 14:
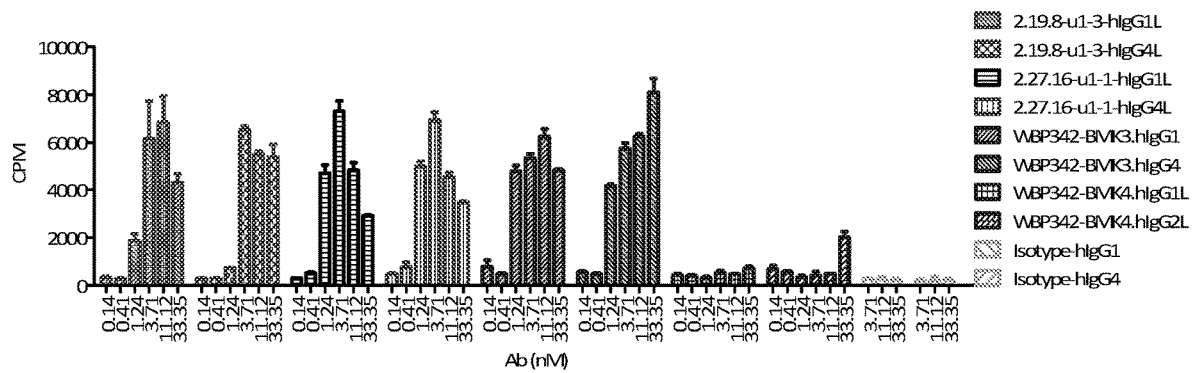
FIG. 14 shows the effect of anti-4-1BB antibodies on proliferation in human $CD8^+$ T cell co-stimulation assay, as assessed by [$^3$H] thymidine incorporation and expressed by CPM, as described in Example 4.9.

As shown in FIG. 13, anti-4-1BB antibodies of the invention (including 2.19.8-u1-3-hIgG1L, 2.19.8-u1-3-hIgG4L, 2.27.16-u1-1-hIgG1L and 2.27.16-u1-1-hIgG4L) increase IFN-7 secretion of human $CD8^+$ T cells. Further, as shown in FIG. 14, the anti-4-1BB antibodies of the invention also promote proliferation of $CD8^+$ T cell.

4.10 ADCC and CDC Test:

In order to assess whether the anti-4-1BB antibodies can trigger Fc effector function upon binding onto 4-1BB expressing cells, the antibodies were evaluated for their ability to mediate antibody-dependent cellular cell-mediated cytotoxicity (ADCC) and complement-dependent cytotoxicity (CDC) activity.

4.10.1 ADCC Test:

Activated human T cells, as target, and various concentrations of anti-4-1BB antibodies were pre-incubated in 96-well round-bottom plate (BD) for 30 minutes; and then allogeneic PBMCs, as effector, were added at the effector/target ratio of 50:1. The plate was kept at 37° C., 5% $CO_2$ for 6 hours. Target cell lysis was determined by LDH-based Cytotoxicity Detection Kit (Roche). The absorbance at 492 nm was read using a microplate reader (Molecular Device).

Figure 15:
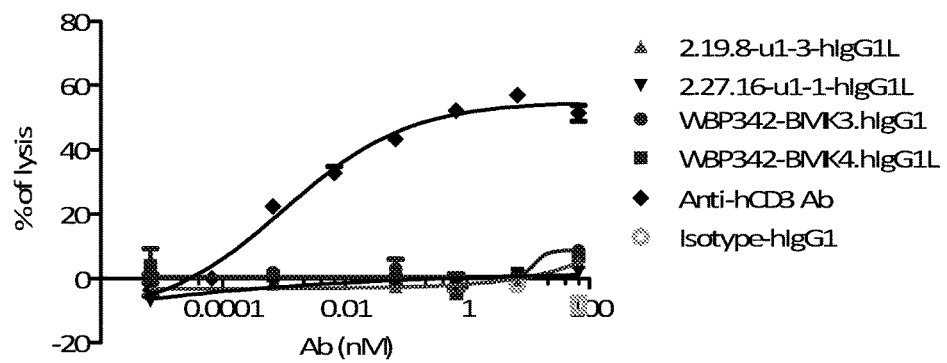
FIG. 15 shows the results of ADCC test of anti-4-1BB antibodies on activated human T cells, as described in Example 4.10.1.

The results in FIG. 15 indicate that the illustrative antibodies 2.19.8-u1-3-hIgG1L and 2.27.16-u1-1-hIgG1L do not mediate ADCC effect on activated human T cells.

4.10.2 CDC Test:

Activated human T cells, as target, and various concentrations of anti-4-1BB antibodies were mixed in 96-well round-bottom plate (BD). Then Human complement was added to each well at a final dilution of 1:50. The plate was kept at 37° C., 5% $CO_2$ for 2 hours. Target cell lysis was determined by CellTiter-Glo (Promega). The luminescence was read using a microplate reader (Molecular Device).

Figure 16:
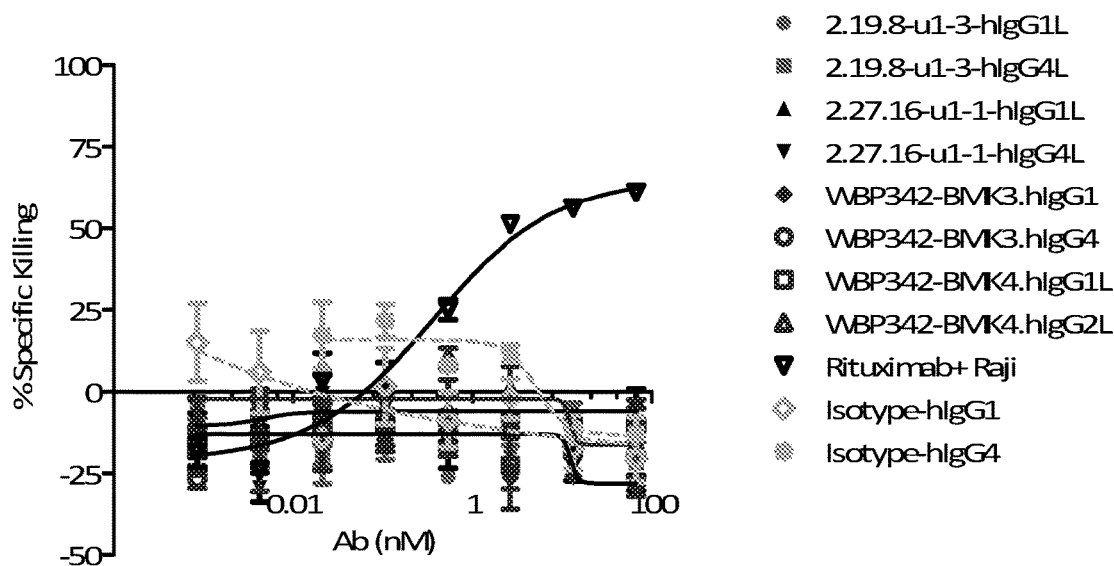
FIG. 16 shows the results of CDC test of anti-4-1BB antibodies on activated human T cells, as described in Example 4.10.2.

The results in FIG. 16 indicate that the illustrative antibodies (including 2.19.8-u1-3-hIgG1L, 2.19.8-u1-3-hIgG4L, 2.27.16-u1-1-hIgG1L and 2.27.16-u1-1-hIgG4L) do not mediate CDC effect on activated human T cells.

Example 5

Epitope Binning and Mapping

Alanine scanning experiments on human 4-1BB were conducted and their effect to antibody binding was evaluated. Alanine residues on human 4-1BB were mutated to glycine codons, and all other residues (except cysteine residues) were mutated to alanine codons. For each residue of the human 4-1BB extracellular domain (ECD), point amino acid substitutions were made using two sequential PCR steps. A pcDNA3.3-h4-1BB_ECD.His plasmid that encodes ECD of human 4-1BB and a C-terminal His-tag was used as template, and a set of mutagenic primer was used for first step PCR using the QuikChange lightning multisite-directed mutagenesis kit (Agilent technologies, Palo Alto, CA). Dpn I endonuclease was used to digest the parental template after mutant strand synthesis reaction. In the second-step PCR, linear DNA expression cassette which composed of a CMV promoter, an extracellular domain (ECD) of 4-1BB, a His-tag and a herpes simplex virus thymidine kinase (TK) polyadenylation was amplified and transiently expressed in 293F cells (Life Technologies, Gaithersburg, MD).

Monoclonal antibodies were coated in plates for ELISA binding assay. After interacting with the supernatant that contains quantified 4-1BB mutant or human 4-1BB_ECD.His protein, HRP conjugated anti-His antibody was added as detection antibody. Absorbance was normalized according to the average of control mutants. After setting an additional cutoff to the binding fold change (<0.75), the final determined epitope residues were identified.

The data was analyzed based on the known structure of the 4-1BB-4-BBL complex (PDB: 6BWV). After setting an additional cutoff to the binding fold change (<0.75) and SASA (solvent accessible surface area; ≥10), the final determined epitope residues were listed in Table 9. SASA values less than 10 indicate that residues are embedded in the protein. There are 12 hot-spot residues to 2.19.8-u1-3-gG1L or 2.19.8-u1-3-.gG4L and 15 residues to 2.27.16-u1-1-IgG1L or 2.27.16-u1-1-IgG4L.

Figure 17:
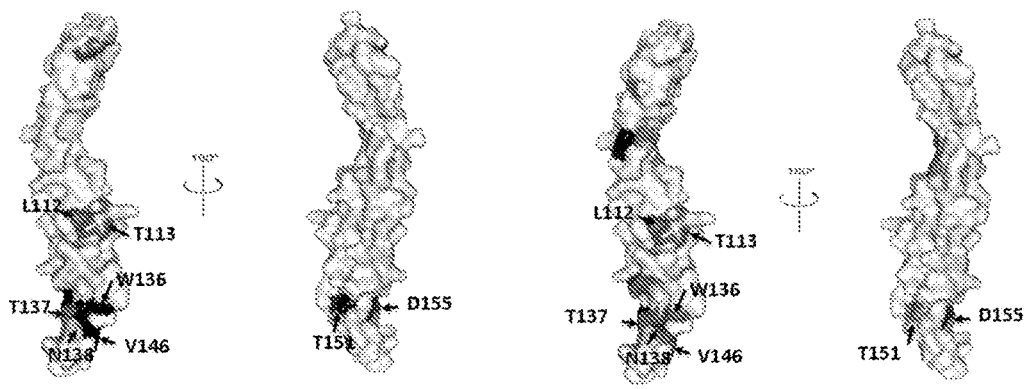
FIG. 17 shows the hot spot residues mapped on human 4-1BB structure, i.e., binding site of antibodies 2.19.8-u1-

All data in Table 9 were therefore mapped on the crystal structure of human 4-1BB to make a better visualization and comparison, which are shown in FIG. 17. FIG. 17 shows the hot spot residues mapped on human 4-1BB structure, i.e., binding site of antibodies 2.19.8-u1-3-IgG1L or 2.19.8-u1-3-IgG4L (FIG. 17A) and 2.27.16-u1-1-IgG1L or 2.27.16-u1-1-IgG4L (FIG. 17B) to human 4-1BB, respectively. Data were from Table 9.

TABLE 9

Identification of the hot-spot residues in charge of the human 4-1BB binding in different locations.

| Human 4-1BB to 2.19.8-u1-3-hIgG1L or 2.19.8-u1-3-hIgG4L [c] | residue location | Human 4-1BB to 2.27.16-u1-1-hIgG1L or 2.27.16-u1-1-h1gG4L [c] | residue location |
|---|---|---|---|
| S 29 | CRD1 | A 33 | CRD1 |
| L 112 | CRD3 | T 35 | CRD1 |
| T 113 | CRD3 | R 66 | CRD2 |
| F 125 | CRD4 | K76 | CRD2 |
| W 136 | CRD4 | N 83 | CRD2 |
| T 137 | CRD4 | D 105 | CRD3 |
| N138 | CRD4 | L 112 | CRD3 |
| V146 | CRD4 | T 113 | CRD3 |
| T151 | CRD4 | R 134 | CRD4 |
| D155 | CRD4 | W 136 | CRD4 |
| L 165 | ATD | T 137 | CRD4 |
| S 170 | ATD | N 138 | CRD4 |
|  |  | V 146 | CRD4 |
|  |  | T 151 | CRD4 |
|  |  | D155A | CRD4 |

Note:
human 4-1BB falls within four cysteine rich domains. CRD1: within amino acids 24 to 45 of human 4-1BB (SEQ ID NO: 21); CRD2: within amino acids 47 to 86 of SEQ ID NO: 21; CRD3: within amino acids 87 to 118 of SEQ ID NO: 21; CRD4: within amino acids 119 to 159 of SEQ ID NO: 21; adjacent transmembrane domain (ATD): within amino acids 160 to 186 of SEQ ID NO: 21. SASA ≥10.
[c] Cutoff fold change < 0.75.

From Table 9, it can be seen that, 2.19.8-u1-3-hIgG1L or 2.19.8-u1-3-hIgG4L has overlapping hot-spot residues with 2.27.16-u1-1-hIgG1L or 2.27.16-u1-1-hIgG4L. All of them comprise the hot-spot residues L112, T113, W136, T137, N138, V146, T151, and D155 of SEQ ID NO:21.

Example 6

In-Vivo Anti-Tumor Activity of 4-1BB Antibodies 6.1 Anti-Tumor Efficacy of Anti-4-1BB Antibodies in Human 4-1BB Knock in Mice Anti-tumor efficacy of 4-1BB monoclonal antibodies (mAbs) were assessed in human 4-1BB knock in mice (B-h4-1BB mice, Biocytogen). B-h4-1BB mice at the age of 8 weeks were inoculated subcutaneously with the mouse colon carcinoma MC38 cell line. Animals were randomized based on tumor size when tumor reached 50-100 mm³. Five administrations of 4-1BB mAbs and isotype control antibody were injected by indicated doses every three days. Tumor size was assessed using caliper measurement twice weekly until study termination.

The results in FIG. 18 show that 4-1BB antibodies with IgG1 or IgG4 (including 2.19.8-u1-3-hIgG1L, 2.19.8-u1-3-hIgG4L, 2.27.16-u1-1-hIgG1L and 2.27.16-u1-1-hIgG4L) effectively inhibited MC38 tumor growth (FIG. 18A). Furthermore, dose-dependent anti-tumor effect was observed in B-h4-1BB transgenic mouse with the treatment of 2.19.8-u1-3-hIgG1L, 2.19.8-u1-3-hIgG4L, 2.27.16-u1-1-hIgG1L and 2.27.16-u1-1-hIgG4L (FIG. 18B, 18C).

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. An isolated antibody against 4-1BB or the antigen-binding portion thereof, wherein the isolated antibody or the antigen-binding portion thereof comprises:
   (a) a CDRH1 comprising SEQ ID NO: 1;
   (b) a CDRH2 comprising SEQ ID NO: 2;
   (c) a CDRH3 comprising SEQ ID NO: 3;
   (d) a CDRL1 comprising SEQ ID NO: 4;
   (e) a CDRL2 comprising SEQ ID NO: 5; and
   (f) a CDRL3 comprising SEQ ID NO: 6.

2. The isolated antibody or the antigen-binding portion thereof of claim 1, wherein the isolated antibody or the antigen-binding portion thereof comprises:
   (A) a heavy chain variable region:
      (i) comprising the amino acid sequence of SEQ ID NO: 13;
      (ii) comprising an amino acid sequence at least 85%, 90%, or 95% identical to SEQ ID NO: 13; or
      (iii) comprising an amino acid sequence with addition, deletion and/or substitution of one or more amino acids compared with SEQ ID NO: 13; and
   (B) a light chain variable region:
      (i) comprising the amino acid sequence of SEQ ID NO: 14;
      (ii) comprising an amino acid sequence at least 85%, at least 90%, or at least 95% identical to SEQ ID NO: 14; or
      (iii) comprising an amino acid sequence with addition, deletion and/or substitution of one or more amino acids compared with SEQ ID NO: 14.

3. The isolated antibody or the antigen-binding portion thereof of claim 1, having one or more of the following properties:
   (a) binding human 4-1BB with a $K_D$ of $2\times10^{-10}$ M or less, as measured by SPR;
   (b) binding cynomolgus 4-1BB with a $K_D$ of $5\times10^{-10}$ M or less, as measured by SPR;
   (c) binding mouse 4-1BB with a $K_D$ of $3\times10^{-8}$ M or less, as measured by SPR;
   (d) inducing production of a cytokine in CD4+ T cells;
   (e) enhancing T cell proliferation;
   (f) binding human, cynomolgus monkey or mouse 4-1BB respectively;
   (g) having no cross-reactivity to human OX40, CD40 or GITR; or
   (h) mediating no ADCC and/or CDC effect on activated human T cells.

4. The isolated antibody or the antigen-binding portion thereof of claim 1, wherein the antibody is a monoclonal antibody, a chimeric antibody, or a humanized antibody.

5. The isolated antibody or the antigen-binding portion thereof of claim 1, wherein the antibody is fused to a constant region of an IgG, selecting from IgG1, IgG2, IgG3, IgG4.

6. An isolated nucleic acid molecule, comprising a nucleic acid sequence encoding the heavy chain variable region and the light chain variable region of the isolated antibody as defined in claim 1.

7. The isolated nucleic acid molecule of claim 6, wherein the isolated nucleic acid molecule encodes the heavy chain variable region of the isolated antibody and comprises a nucleic acid sequence selected from the group consisting of:
   (A) a nucleic acid sequence that encodes a heavy chain variable region as set forth in SEQ ID NO: 13; or
   (B) a nucleic acid sequence as set forth in SEQ ID NO: 17.

8. The isolated nucleic acid molecule of claim 6, wherein the isolated nucleic acid molecule encodes the light chain variable region of the isolated antibody and comprises a nucleic acid sequence selected from the group consisting of:
   (A) a nucleic acid sequence that encodes a light chain variable region as set forth in SEQ ID NO: 14; or
   (B) a nucleic acid sequence as set forth in SEQ ID NO: 18.

9. A vector comprising the isolated nucleic acid molecule of claim 6.

10. A host cell comprising the vector of claim 9.

11. A pharmaceutical composition comprising at least one antibody or antigen-binding portion thereof as defined in claim 1 and a pharmaceutically acceptable carrier.

12. A method for preparing antibody or antigen-binding portion thereof as defined in claim 1, comprising the steps of: expressing the antibody or antigen-binding portion thereof as defined in claim 1 in the host cell comprising a vector which comprises an isolated nucleic acid molecule encoding the heavy chain variable region and the light chain variable region of the isolated antibody as defined in claim 1; and isolating the antibody or antigen-binding portion thereof from the host cell.

13. A method for modulating an immune response in a subject, comprising administering to the individual an effective amount of the antibody or antigen-binding portion thereof as defined in claim 1 to the subject.

14. A kit comprising a container comprising at least one antibody or antigen-binding portion thereof as defined in claim 1.

* * * * *

SEQUENCE LISTING

<160> NUMBER OF SEQ ID NOS: 22

<210> SEQ ID NO 1
<211> LENGTH: 10
<212> TYPE: PRT
<213> ORGANISM: Artificial Sequence
<220> FEATURE:
<223> OTHER INFORMATION: CDRH1 of "2.19.8-u1-3-hIgG1L" or "2.19.8-u1-3-hIgG4L"

<400> SEQUENCE: 1

Gly Phe Thr Phe Ser Asp Tyr Phe Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDRH2 of "2.19.8-u1-3-hIgG1L" or "2.19.8-u1-3-hIgG4L"

<400> SEQUENCE: 2

Tyr Ile Ser Asn Ala Gly Ser Ser Lys Tyr Tyr Ala Asp Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: CDRH3 of "2.19.8-u1-3-hIgG1L" or "2.19.8-u1-3-hIgG4L"

<400> SEQUENCE: 3

Asp Pro Tyr Ser Gly Ser Tyr Ser Gly Trp Phe Asp Pro
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CDRL1 of "2.19.8-u1-3-hIgG1L" or "2.19.8-u1-3-hIgG4L"

<400> SEQUENCE: 4

Ser Gly Asp Asp Leu Gly Asp Lys Tyr Thr Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDRL2 of "2.19.8-u1-3-hIgG1L" or "2.19.8-u1-3-hIgG4L"

<400> SEQUENCE: 5

Gln Asp His Lys Arg Pro Ser
1               5

<210> SEQ ID NO 6
<211> LENGTH: 9
<212> TYPE: PRT
<213> ORGANISM: Artificial Sequence

```
<220> FEATURE:
<223> OTHER INFORMATION: CDRL3 of "2.19.8-u1-3-hIgG1L" or "2.19.8-u1-3-
      hIgG4L"

<400> SEQUENCE: 6

Gln Ala Trp Asp Lys Gly Ile Val Val
1               5

<210> SEQ ID NO 7
<211> LENGTH: 12
<212> TYPE: PRT
<213> ORGANISM: Artificial Sequence
<220> FEATURE:
<223> OTHER INFORMATION: CDRH1 of "2.27.16-u1-1-hIgG1L" or "2.27.16-u1-
      1-hIgG4L"

<400> SEQUENCE: 7

Gly Gly Ser Ile Asn Ser Gln Gly Tyr Tyr Trp Ser
1               5                   10

<210> SEQ ID NO 8
<211> LENGTH: 16
<212> TYPE: PRT
<213> ORGANISM: Artificial Sequence
<220> FEATURE:
<223> OTHER INFORMATION: CDRH2 of "2.27.16-u1-1-hIgG1L" or "2.27.16-u1-
      1-hIgG4L"

<400> SEQUENCE: 8

Tyr Ile Tyr Asp Ser Gly Ser Ala Tyr Tyr Asn Pro Ser Leu Glu Arg
1               5                   10                  15

<210> SEQ ID NO 9
<211> LENGTH: 9
<212> TYPE: PRT
<213> ORGANISM: Artificial Sequence
<220> FEATURE:
<223> OTHER INFORMATION: CDRH3 of "2.27.16-u1-1-hIgG1L" or "2.27.16-u1-
      1-hIgG4L"

<400> SEQUENCE: 9

Ile Val Ala Ala Gly Arg Ile Asp Pro
1               5

<210> SEQ ID NO 10
<211> LENGTH: 11
<212> TYPE: PRT
<213> ORGANISM: Artificial Sequence
<220> FEATURE:
<223> OTHER INFORMATION: CDRL1 of "2.27.16-u1-1-hIgG1L" or "2.27.16-u1-
      1-hIgG4L"

<400> SEQUENCE: 10

Gly Gly Asp Asn Ile Gly Ile Lys Ile Val His
1               5                   10

<210> SEQ ID NO 11
<211> LENGTH: 7
<212> TYPE: PRT
<213> ORGANISM: Artificial Sequence
<220> FEATURE:
<223> OTHER INFORMATION: CDRL2 of "2.27.16-u1-1-hIgG1L" or "2.27.16-u1-
      1-hIgG4L"

<400> SEQUENCE: 11

Asp Asp Asn Asp Arg Pro Ser
1               5
```

```
<210> SEQ ID NO 12
<211> LENGTH: 11
<212> TYPE: PRT
<213> ORGANISM: Artificial Sequence
<220> FEATURE:
<223> OTHER INFORMATION: CDRL3 of "2.27.16-u1-1-hIgG1L" or "2.27.16-u1-
      1-hIgG4L"

<400> SEQUENCE: 12

Gln Val Trp Asp Arg Arg Ser Asp His Val Val
1               5                   10

<210> SEQ ID NO 13
<211> LENGTH: 122
<212> TYPE: PRT
<213> ORGANISM: Artificial Sequence
<220> FEATURE:
<223> OTHER INFORMATION: VH of "2.19.8-u1-3-hIgG1L" or "2.19.8-u1-3-
      hIgG4L"

<400> SEQUENCE: 13

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Ile Arg Gln Ala Pro Gly Lys Gly Leu Glu Trp Val
        35                  40                  45

Ser Tyr Ile Ser Asn Ala Gly Ser Ser Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Pro Tyr Ser Gly Ser Tyr Ser Gly Trp Phe Asp Pro Trp
            100                 105                 110

Gly Gln Gly Thr Leu Val Thr Val Ser Ser
        115                 120

<210> SEQ ID NO 14
<211> LENGTH: 106
<212> TYPE: PRT
<213> ORGANISM: Artificial Sequence
<220> FEATURE:
<223> OTHER INFORMATION: VL of "2.19.8-u1-3-hIgG1L" or "2.19.8-u1-3-
      hIgG4L"

<400> SEQUENCE: 14

Ser Tyr Asp Leu Thr Gln Pro Pro Ser Val Ser Val Ser Pro Gly Gln
1               5                   10                  15

Thr Ala Ser Ile Thr Cys Ser Gly Asp Asp Leu Gly Asp Lys Tyr Thr
            20                  25                  30

Ser Trp Tyr Gln Gln Lys Pro Gly Gln Ser Pro Val Leu Val Val Tyr
        35                  40                  45

Gln Asp His Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Lys Gly Ile Val Val
                85                  90                  95

Phe Gly Gly Gly Thr Lys Leu Thr Val Leu
```

-continued

<210> SEQ ID NO 15
<211> LENGTH: 119
<212> TYPE: PRT
<213> ORGANISM: Artificial Sequence
<220> FEATURE:
<223> OTHER INFORMATION: VH of "2.27.16-u1-1-hIgG1L" or "2.27.16-u1-1-
      hIgG4L"

<400> SEQUENCE: 15

Gln Glu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gln
            20                  25                  30

Gly Tyr Tyr Trp Ser Trp Ile Arg Gln His Pro Gly Lys Gly Leu Glu
        35                  40                  45

Trp Ile Gly Tyr Ile Tyr Asp Ser Gly Ser Ala Tyr Tyr Asn Pro Ser
    50                  55                  60

Leu Glu Arg Arg Val Ala Ile Ser Leu Asp Thr Ser Lys Asn Gln Phe
65                  70                  75                  80

Ser Leu Asn Leu Asn Ser Val Thr Val Ala Asp Thr Ala Val Tyr Tyr
                85                  90                  95

Cys Ala Arg Ile Val Ala Ala Gly Arg Ile Asp Pro Trp Gly Gln Gly
            100                 105                 110

Thr Leu Val Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: VL of "2.27.16-u1-1-hIgG1L" or "2.27.16-u1-1-
      hIgG4L"

<400> SEQUENCE: 16

Ser Tyr Val Leu Thr Gln Pro Pro Ser Val Ser Val Ala Pro Gly Gln
1               5                   10                  15

Thr Ala Arg Met Thr Cys Gly Gly Asp Asn Ile Gly Ile Lys Ile Val
            20                  25                  30

His Trp Tyr Gln Gln Lys Ala Gly Gln Ala Pro Val Leu Val Val Tyr
        35                  40                  45

Asp Asp Asn Asp Arg Pro Ser Gly Ile Pro Asp Arg Phe Ser Gly Ser
    50                  55                  60

Asn Ser Gly Asn Thr Ala Thr Leu Thr Ile Ser Arg Val Ala Ala Gly
65                  70                  75                  80

Asp Glu Ala Asp Tyr Tyr Cys Gln Val Trp Asp Arg Arg Ser Asp His
                85                  90                  95

Val Val Phe Gly Gly Gly Thr Lys Leu Thr Val Leu
            100                 105

<210> SEQ ID NO 17
<211> LENGTH: 366
<212> TYPE: DNA
<213> ORGANISM: Artificial Sequence
<220> FEATURE:
<223> OTHER INFORMATION: DNA sequence encoding VH of "2.19.8-u1-3-
      hIgG1L" or "2.19.8-u1-3-hIgG4L"

<400> SEQUENCE: 17

```
caggtgcaac tggtggagtc tgggggaggc ttggtcaagc ctggagggtc cctgagactg    60
tcctgtgcag cctctggatt caccttcagt gactacttca tgagctggat ccgccaggct   120
ccagggaagg ggctggaatg ggtttcatac attagtaatg ccggtagttc caaatattat   180
gcagactccg tgaagggccg attcaccatc tccaggaca acgccaagaa ctcactgtat    240
ctgcaaatga acagtctgag agccgaggac acggccgtgt attactgtgt gagagatcct   300
tatagtggga gttactccgg gtggttcgac ccctggggcc agggaaccct ggtcaccgtc   360
tcctca                                                              366
```

```
<210> SEQ ID NO 18
<211> LENGTH: 318
<212> TYPE: DNA
<213> ORGANISM: Artificial Sequence
<220> FEATURE:
<223> OTHER INFORMATION: DNA sequence encoding VL of "2.19.8-u1-3-
      hIgG1L" or "2.19.8-u1-3-hIgG4L"

<400> SEQUENCE: 18
tcctatgacc tgactcagcc accctcagtg tccgtgtccc caggacagac agccagcatc    60
acctgttctg gagatgattt gggagataaa tatactagct ggtatcagca gaagccgggc   120
cagtcccctg tattggtcgt ctatcaagat cacaagcggc cctcagggat ccctgagcga   180
ttctctggct ccaattctgg gaacacagcc actctgacca tcagcgggac ccaggctatg   240
gatgaggctg actattactg tcaggcgtgg gacaagggca ttgtggtatt cggcggaggg   300
accaaactga ccgtccta                                                 318
```

```
<210> SEQ ID NO 19
<211> LENGTH: 357
<212> TYPE: DNA
<213> ORGANISM: Artificial Sequence
<220> FEATURE:
<223> OTHER INFORMATION: DNA sequence encoding VH of "2.27.16-u1-1-
      hIgG1L" or "2.27.16-u1-1-hIgG4L"

<400> SEQUENCE: 19
caggagcagc tgcaggagtc gggcccagga ctggtgaagc cttcacagac cttgtccctc    60
acctgcactg tctctggtgg ctccatcaac agtcagggtt actactggag ctggatccgc   120
cagcacccag gaagggcct ggagtggatt gggtacatct atgacagtgg aagtgcctac    180
tacaatccgt ccctcgagag gcgagttgcc atatcattag acacgtctaa gaaccagttc   240
tccctgaacc tgaactctgt gactgtcgcg gacacggccg tttattactg cgcgaggata   300
gtagcagctg gtcggatcga cccctggggc cagggaaccc tggtcaccgt ctcctca     357
```

```
<210> SEQ ID NO 20
<211> LENGTH: 324
<212> TYPE: DNA
<213> ORGANISM: Artificial Sequence
<220> FEATURE:
<223> OTHER INFORMATION: DNA sequence encoding VL of "2.27.16-u1-1-
      hIgG1L" or "2.27.16-u1-1-hIgG4L"

<400> SEQUENCE: 20
tcctatgtcc tgactcagcc accctcggtg tcagtggccc ccggacagac ggccaggatg    60
acctgtgggg gagacaacat tggaattaaa attgtgcact ggtaccagca gaaggcaggc   120
caggcccctg tgttggtcgt ctatgatgat aatgaccggc cctcagggat ccctgaccga   180
ttctctggct ccaactctgg gaacacggcc accctgacca tcagcagggt cgcagccggg   240
```

```
gatgaggccg actactactg tcaggtgtgg gataggagga gtgatcatgt ggttttcggc      300
ggagggacca agttgaccgt ccta                                              324
```

<210> SEQ ID NO 21
<211> LENGTH: 255
<212> TYPE: PRT
<213> ORGANISM: Artificial Sequence
<220> FEATURE:
<223> OTHER INFORMATION: Amino acid sequence of full-length human 4-1BB

<400> SEQUENCE: 21

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 22
<211> LENGTH: 163
<212> TYPE: PRT
<213> ORGANISM: Artificial Sequence
<220> FEATURE:
<223> OTHER INFORMATION: Amino acid sequence of extracellular domain of
      human 4-1BB

<400> SEQUENCE: 22

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

```
Ala Gly Gly Gln Arg Thr Cys Asp Ile Cys Arg Gln Cys Lys Gly Val
        35                  40                  45
Phe Arg Thr Arg Lys Glu Cys Ser Ser Thr Ser Asn Ala Glu Cys Asp
    50                  55                  60
Cys Thr Pro Gly Phe His Cys Leu Gly Ala Gly Cys Ser Met Cys Glu
65              70                  75                  80
Gln Asp Cys Lys Gln Gly Gln Glu Leu Thr Lys Lys Gly Cys Lys Asp
            85                  90                  95
Cys Cys Phe Gly Thr Phe Asn Asp Gln Lys Arg Gly Ile Cys Arg Pro
                100                 105                 110
Trp Thr Asn Cys Ser Leu Asp Gly Lys Ser Val Leu Val Asn Gly Thr
            115                 120                 125
Lys Glu Arg Asp Val Val Cys Gly Pro Ser Pro Ala Asp Leu Ser Pro
        130                 135                 140
Gly Ala Ser Ser Val Thr Pro Pro Ala Pro Ala Arg Glu Pro Gly His
145                 150                 155                 160
Ser Pro Gln
```